United States Patent [19]

Heller et al.

[11] Patent Number: 5,929,208
[45] Date of Patent: Jul. 27, 1999

[54] METHODS FOR ELECTRONIC SYNTHESIS OF POLYMERS

[75] Inventors: Michael J. Heller, Encinitas; Eugene Tu, San Diego, both of Calif.

[73] Assignee: Nanogen, Inc., Del Mar, Calif.

[21] Appl. No.: 08/725,976

[22] Filed: Oct. 4, 1996

Related U.S. Application Data

[63] Continuation of application No. 08/146,504, Nov. 1, 1993, Pat. No. 5,605,662.

[51] Int. Cl.$^6$ ............................ A61K 38/00; C07H 21/00
[52] U.S. Cl. ............................ 530/333; 422/50; 422/62; 422/68.1; 422/69; 422/82.05; 422/129; 422/131; 422/134; 435/283.1; 435/285.1; 435/285.2; 435/286.1; 435/286.2; 435/287.1; 435/287.2; 435/287.9; 435/288.3; 435/289.1; 435/299.1; 435/305.1; 530/334; 536/25.3
[58] Field of Search ............................ 435/69.1, 283.1, 435/285.1, 285.2, 286.1, 286.2, 287.1, 287.2, 287.9, 288.3, 289.1, 299.1, 305.1; 530/333, 334; 536/25.3; 422/50, 62, 68.1, 69, 82.05, 129, 131, 134

[56] References Cited

U.S. PATENT DOCUMENTS

| | | | |
|---|---|---|---|
| 3,950,738 | 4/1976 | Hayashi et al. | 340/173 LS |
| 3,995,190 | 11/1976 | Salgo | 313/391 |
| 4,563,419 | 1/1986 | Ranki et al. | 435/6 |
| 4,580,895 | 4/1986 | Patel | 356/39 |
| 4,584,075 | 4/1986 | Goldstein | 204/182.3 |
| 4,594,135 | 6/1986 | Goldstein | 204/180.1 |
| 4,751,177 | 6/1988 | Stabinsky | 435/6 |
| 4,787,963 | 11/1988 | MacConnell | 204/180.1 |
| 4,816,418 | 3/1989 | Mack et al. | 436/518 |
| 4,822,566 | 4/1989 | Newman | 422/68 |
| 4,828,979 | 5/1989 | Klevan et al. | 435/6 |
| 4,908,112 | 3/1990 | Pace | 204/299 R |
| 5,063,081 | 11/1991 | Cozzette et al. | 427/2 |
| 5,074,977 | 12/1991 | Cheung et al. | 204/153.1 |
| 5,075,077 | 12/1991 | Durley, III et al. | 422/56 |

(List continued on next page.)

FOREIGN PATENT DOCUMENTS

| | | |
|---|---|---|
| 0228075 | 7/1987 | European Pat. Off. . |
| 2156074 | 10/1985 | United Kingdom . |
| 2247889 | 3/1992 | United Kingdom . |
| 8603782 | 7/1986 | WIPO . |
| WO88/08528 | 11/1988 | WIPO . |
| WO89/01159 | 2/1989 | WIPO . |
| 8910977 | 11/1989 | WIPO . |
| 9001564 | 2/1990 | WIPO . |
| WO92/044770 | 3/1992 | WIPO . |
| 93/22678 | 11/1993 | WIPO . |
| WO95/07363 | 3/1995 | WIPO . |
| 57087 | of 1987 | Yugoslavia . |

OTHER PUBLICATIONS

Anand and Southern, "Pulsed field gel electrophoresis," *Gel Electrophoresis of Nucleic Acids—A Practical Approach*, 2d edition, eds. D. Rickwood and B.D. Hames, (New York:IRL Press 1990) pp. 101–123.

(List continued on next page.)

*Primary Examiner*—Ardin H. Marschel
*Attorney, Agent, or Firm*—Lyon & Lyon LLP

[57] ABSTRACT

A self-addressable, self-assembling microelectronic device is designed and fabricated to actively carry out and control multi-step and multiplex molecular biological reactions in microscopic formats. These reactions include nucleic acid hybridization, antibody/antigen reaction, diagnostics, and biopolymer synthesis. The device can be fabricated using both microlithographic and micro-machining techniques. The device can electronically control the transport and attachment of specific binding entities to specific micro-locations. The specific binding entities include molecular biological molecules such as nucleic acids and polypeptides. The device can subsequently control the transport and reaction of analytes or reactants at the addressed specific micro-locations. The device is able to concentrate analytes and reactants, remove non-specifically bound molecules, provide stringency control for DNA hybridization reactions, and improve the detection of analytes. The device can be electronically replicated.

22 Claims, 16 Drawing Sheets

U.S. PATENT DOCUMENTS

| | | | |
|---|---|---|---|
| 5,096,669 | 3/1992 | Lauks et al. | 422/61 |
| 5,096,807 | 3/1992 | Leaback | 435/6 |
| 5,125,748 | 6/1992 | Bjornson et al. | 356/414 |
| 5,126,022 | 6/1992 | Soane et al. | 204/180.1 |
| 5,143,854 | 9/1992 | Pirrung et al. | 436/518 |
| 5,164,319 | 11/1992 | Hafeman et al. | 435/291 |
| 5,166,063 | 11/1992 | Johnson | 435/173 |
| 5,200,051 | 4/1993 | Cozzette et al. | 204/403 |
| 5,202,231 | 4/1993 | Drmanac et al. | 435/6 |
| 5,219,726 | 6/1993 | Evans | 435/6 |
| 5,227,265 | 7/1993 | DeBoer et al. | 430/41 |
| 5,234,566 | 8/1993 | Osman et al. | 204/403 |
| 5,304,487 | 4/1994 | Wilding et al. | 435/291 |
| 5,312,527 | 5/1994 | Mikkelsen et al. | 204/153.12 |
| 5,434,049 | 7/1995 | Okano et al. | 435/6 |
| 5,527,670 | 6/1996 | Stanley | 435/6 |
| 5,653,939 | 8/1997 | Hollis et al. | 422/50 |
| 5,681,751 | 10/1997 | Begg et al. | 436/89 |

OTHER PUBLICATIONS

Anderson and Young, "Quantitative Filter Hybridisation," *Nucleic Acid Hybridization—A Practical Approach*, eds. B.D. Hames and S.J. Higgins (Washington DC:IRL Press 1985) pp. 73–111.

Bains, "Setting a Sequence to Sequence a Sequence," *Bio/Technology*, 10:757–758 (1992).

Barinaga, "Will 'DNA Chip' Speed Genome Initiative?" *Science*, 253:1489 (1991).

Beattie et al., "Genosensor Technology," *The 1992 San Diego Conference: Genetic Recognition*, pp. 1–5, (Nov., 1992).

Beltz et al., "Isolation of Multigene Families and Determination of Homologies by Filter Hybridization Methods," *Methods in Enzymology*, 100:266–285 (1983).

Connor et al., "Detection of sickle cell $\beta^3$–globin allele by hybridization with synthetic oligonucleotides," *Proc. Natl. Acad. Sci. USA*, 80:278–282 (1983).

Drmanac et al., "Sequencing of Megabase Plus DNA by Hybridization: Theory of the Method," *Genomics*, 4:114–128 (1989).

Drmanac et al., "DNA Sequence Determination by Hybridization: A Strategy for Efficient Large–Scale Sequencing," 260:1649–1652 (1993).

Fodor et al., "Multiplexed biochemical assays with biological chips," *Nature*, 364:555–556 (1993).

Fodor et al., "Light–Directed, Spatially Addressable Parallel Chemical Synthesis," *Science*, 251:767–773 (1991).

Horejsi, "Some Theoretical Aspects of Affinity Electrophoresis," *Journal of Chromatography*, 178:1–13 (1979).

Horejsi et al., "Determination of Dissociation Constants of Lectin Sugar Complexes by Means of Affinity Electrophoresis," *Biochimica et biophysica acta*, 499:290–300 (1977).

Ranki et al., "Sandwich hybridization as a convenient method for the detection of nucleic acids in crude samples," *Gene*, 21:77–85 (1983).

Saiki, "Amplification of Genomic DNA," *PCR Protocols: A Guide to Methods and Applications*, (Academic Press, Inc. 1990) pp. 13–20.

Southern et al., "Analyzing and Comparing Nucleic Acid Sequences by Hybridization to Arrays of Oligonucleotides: Evaluation Using Experimental Models," *Genomics*, 13:1008–1017 (1992).

Strezoska et al., "DNA sequencing by hybridization: 100 bases read by a non–gel–based method," *Proc. Natl. Acad. Sci. USA*, 88:100898–10093 (1991).

Wallace et al., "Hybridization of synthetic oligodcoxyribonucleotides to $\Phi_x$ 174 DNA: the effect of single base pair mismatch," *Nucleic Acid Res.*, 6:3543–3557 (1979).

Washizu, "Electrostatic manipulation of biological objects," *Journal of Electrostatics*, 25:109–123 (1990).

Washizu and Kurosawa, "Electrostatic Manipulation of DNA in Microfabricated Structures," *IEEE Transactions on Industry Applications*, 26:1165–1172 (1990).

Brown et al, "Electrochemically Induced Adsorption of Radio–Labelled DNA on Gold and HOPG Substrates for STM Investigations", Ultramicroscopy 38 (1991) 253–264.

Washizu, et al, "Electrostatic Manipulation of DNA in Microfabricated Structures", IEEE Transactions on Industrial Applications, vol. 26, No. 6, Nov./Dec., 1990, pp. 1165–1172.

Palecek, "New Trends in Electrochemical Analysis of Nucleic Acids", Bioelectrochemistry and Bioenergetics, 20 (1988), pp. 179–194.

BioChip Technology Development, Lincoln Laboratory Technical Report 901, Nov. 9, 1990.

Abrams et al., "Comprehensive Detection of Single Base Changes in Human Genomic DNA Using Denaturing Gradient Gel Electrophoresis and a GC Clamp", Genomics, vol. 7, 1990, pp. 463–475.

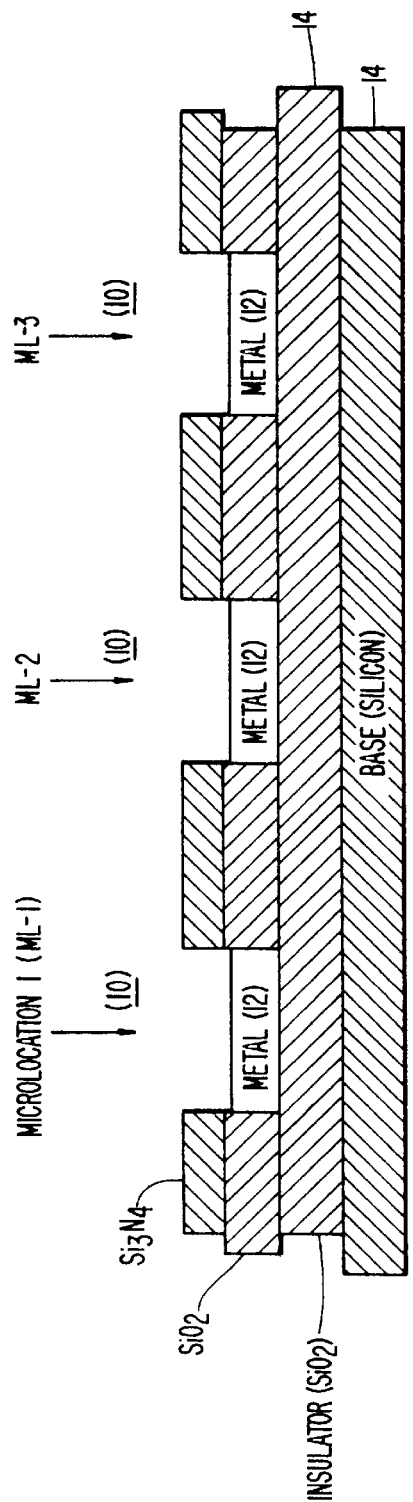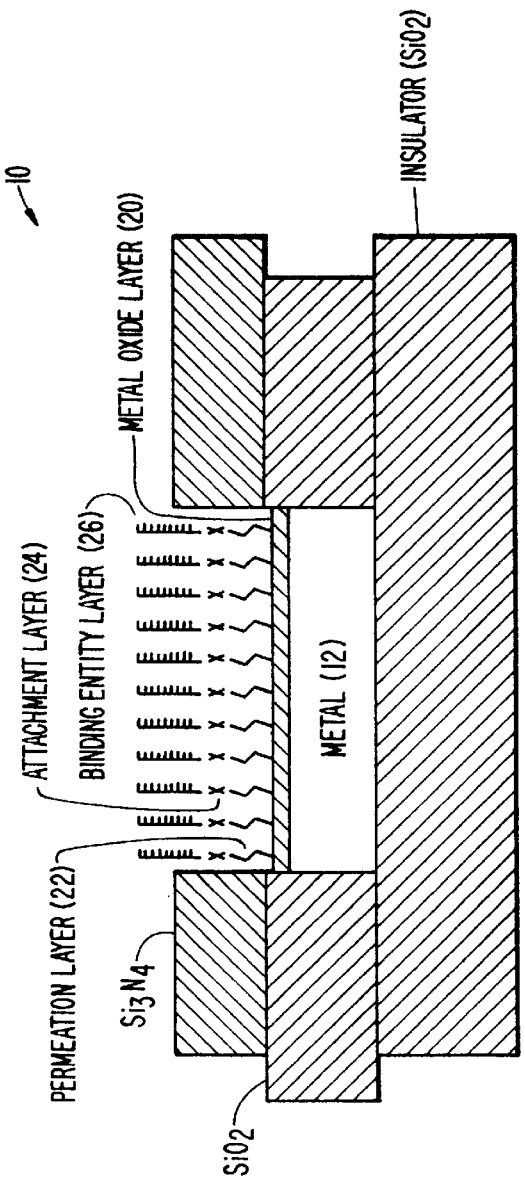

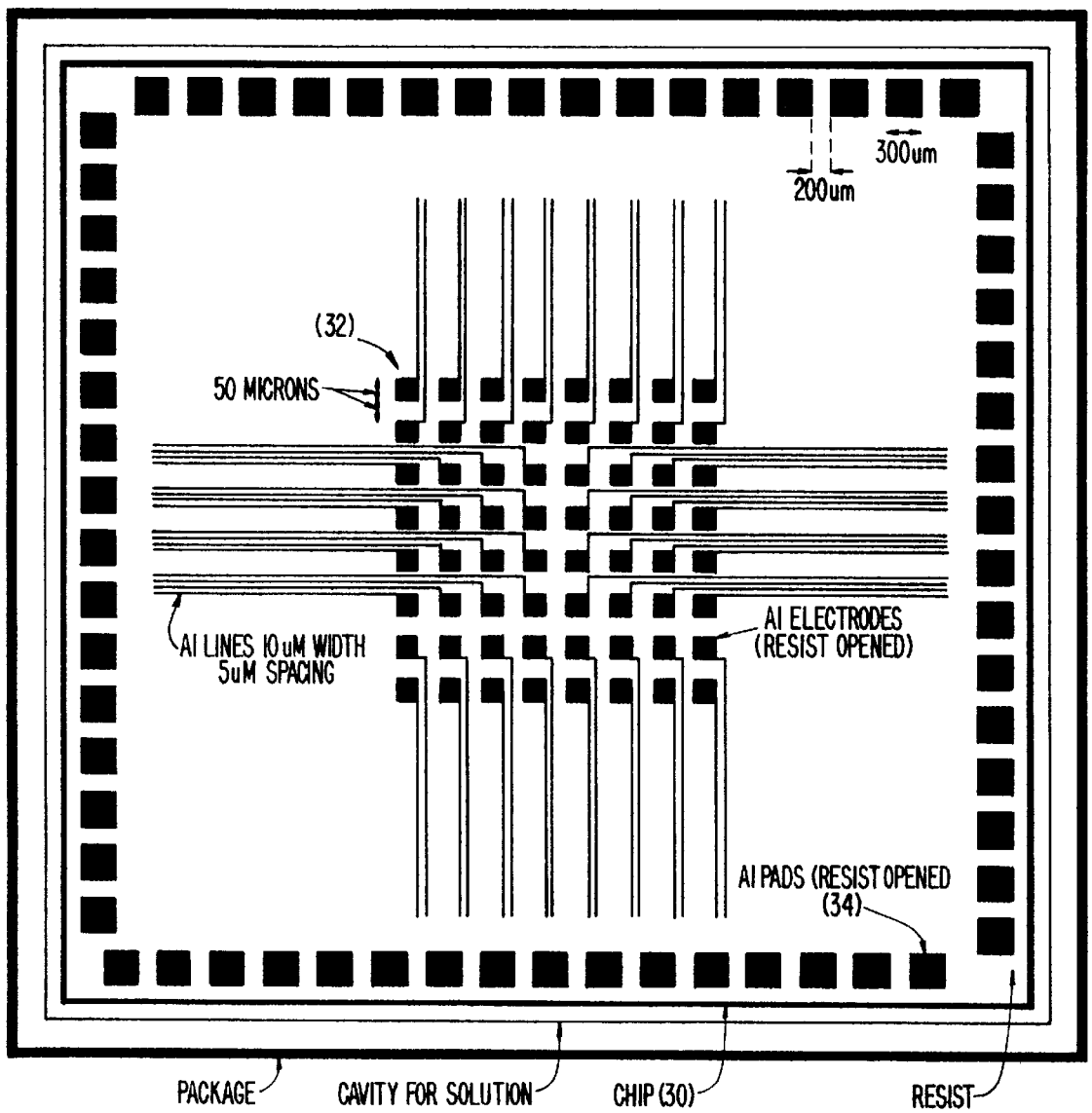

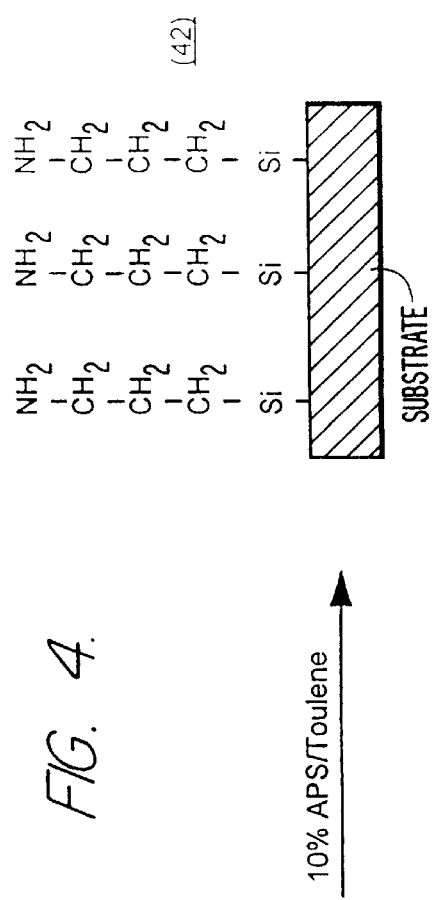
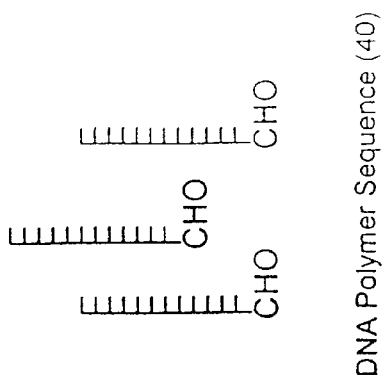
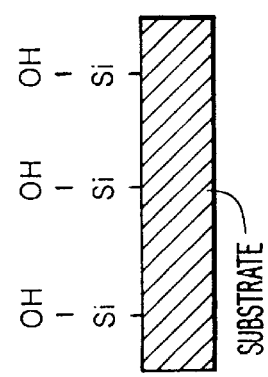
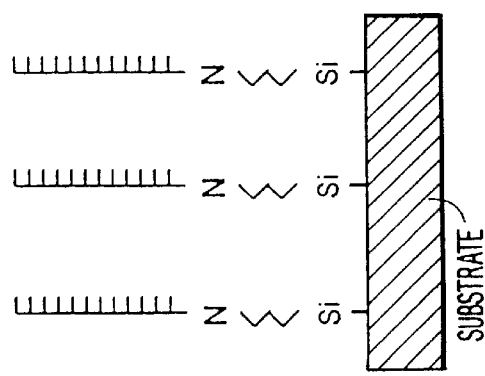
FIG. 4.

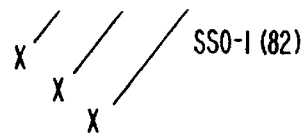
FIG. 8a.
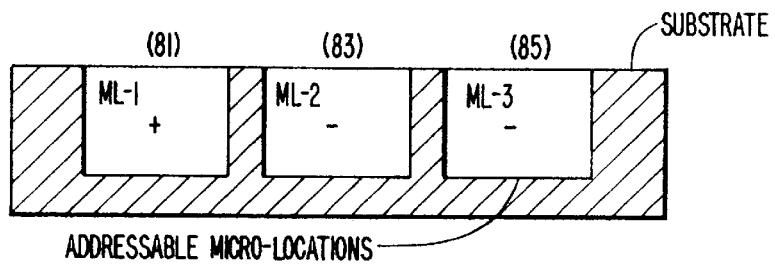
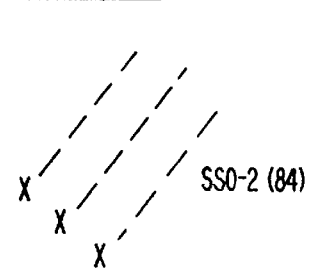
FIG. 8b.
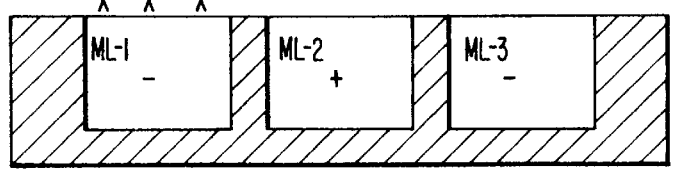
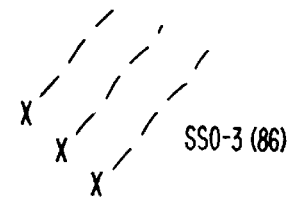
FIG. 8c.
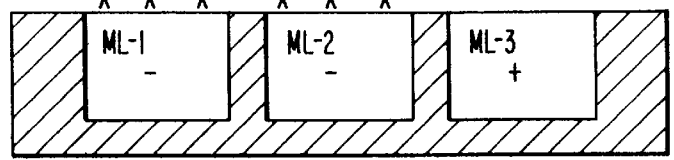
FIG. 8d.
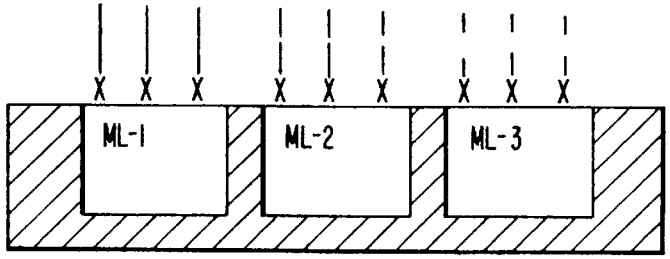

FIG. 13a.
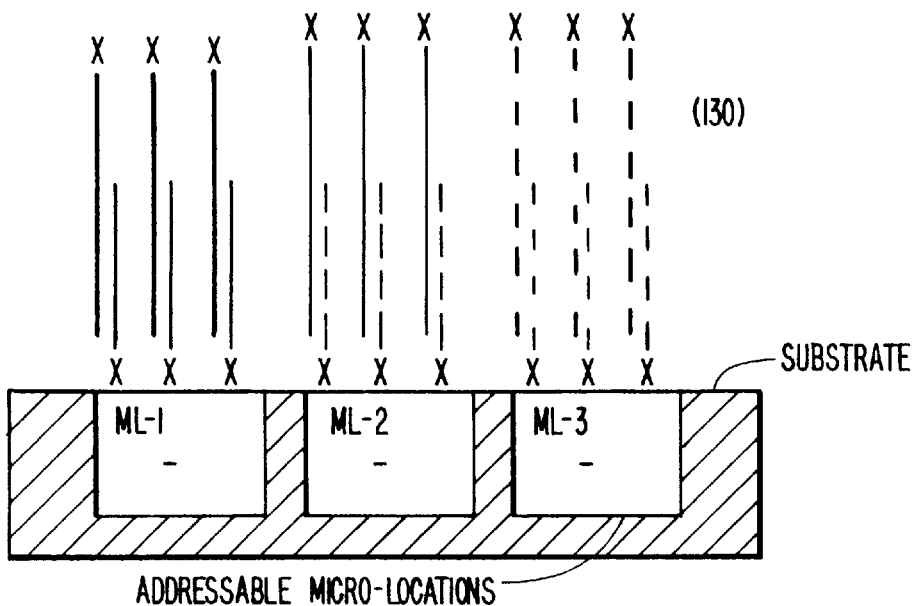
FIG. 13b.
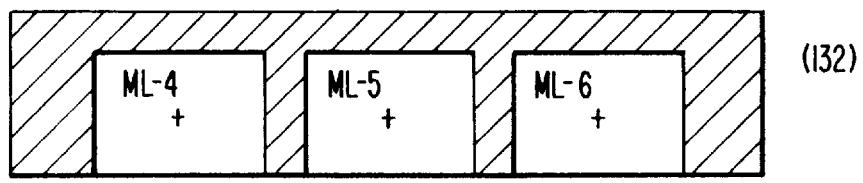
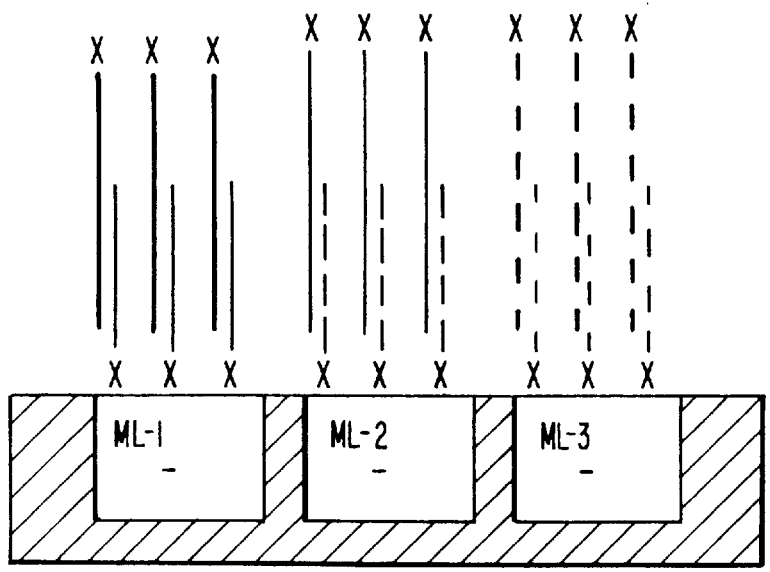

METHODS FOR ELECTRONIC SYNTHESIS OF POLYMERS

This is a continuation of application Ser. No. 08/146,504, filed on Nov. 1, 1993, now U.S. Pat. No. 5,605,662.

FIELD OF THE INVENTION

This invention pertains to the design, fabrication, and uses of a self-addressable, self-assembling microelectronic system which can actively carry out and control multi-step and multiplex reactions in microscopic formats. In particular, these reactions include molecular biological reactions, such as nucleic acid hybridizations, antibody/antigen reactions, clinical diagnostics, and biopolymer synthesis.

BACKGROUND OF THE INVENTION

Molecular biology comprises a wide variety of techniques for the analysis of nucleic acid and protein, many of which form the basis of clinical diagnostic assays. These techniques include nucleic acid hybridization analysis, restriction enzyme analysis, genetic sequence analysis, and separation and purification of nucleic acids and proteins (See, e.g., J. Sambrook, E. F. Fritsch, and T. Maniatis, *Molecular Cloning: A Laboratory Manual*, 2 Ed., Cold Spring Harbor Laboratory Press, Cold Spring Harbor, N.Y., 1989).

Most molecular biology techniques involve carrying out numerous operations (e.g., pipetting) on a large number of samples. They are often complex and time consuming, and generally require a high degree of accuracy. Many a technique is limited in its application by a lack of sensitivity, specificity, or reproducibility. For example, problems with sensitivity and specificity have so far limited the application of nucleic acid hybridization.

Nucleic acid hybridization analysis generally involves the detection of a very small numbers of specific target nucleic acids (DNA or RNA) with probes among a large amount of non-target nucleic acids. In order to keep high specificity, hybridization is normally carried out under the most stringent condition, achieved through a combination of temperature, salts, detergents, solvents, chaotropic agents, and denaturants.

Multiple sample nucleic acid hybridization analysis has been conducted on a variety of filter and solid support formats (see G. A. Beltz et al., in *Methods in Enzymology*, Vol. 100, Part B, R. Wu, L. Grossmam, K. Moldave, Eds., Academic Press, New York, Chapter 19, pp. 266–308, 1985). One format, the so-called "dot blot" hybridization, involves the non-covalent attachment of target DNAs to a filter, which are subsequently hybridized with a radioisotope labeled probe(s). "Dot blot" hybridization gained widespread use, and many versions were developed (see M. L. M. Anderson and B. D. Young, in *Nucleic Acid Hybridization—A Practical Approach*, B. D. Hames and S. J. Higgins, Eds., IRL Press, Washington D.C., Chapter 4, pp. 73–111, 1985). It has been developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

Another format, the so-called "sandwich" hybridization, involves attaching oligonucleotide probes covalently to a solid support and using them to capture and detect multiple nucleic acid targets. (M. Ranki et al., Gene, 21, pp. 77–85, 1983; A. M. Palva, T. M. Ranki, and H. E. Soderlund, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751,177, Jan. 14, 1988; T. H. Adams et al., in PCT WO 90/01564, Feb. 22, 1990; R. B. Wallace et al. 6 Nucleic Acid Res. 11, p. 3543, 1979; and B. J. Connor et al., 80 Proc. Natl. Acad. Sci. USA pp. 278–282, 1983).

Using the current nucleic acid hybridization formats and stringency control methods, it remains difficult to detect low copy number (i.e., 1–100,000) nucleic acid targets even with the most sensitive reporter groups (enzyme, fluorophores, radioisotopes, etc.) and associated detection systems (fluorometers, luminometers, photon counters, scintillation counters, etc.).

This difficulty is caused by several underlying problems associated with direct probe hybridization. The first and the most serious problem relates to the stringency control of hybridization reactions. Hybridization reactions are usually carried out under the most stringent conditions in order to achieve the highest degree of specificity. Methods of stringency control involve primarily the optimization of temperature, ionic strength, and denaturants in hybridization and subsequent washing procedures. Unfortunately, the application of these stringency conditions causes a significant decrease in the number of hybridized probe/target complexes for detection.

The second problem relates to the high complexity of DNA in most samples, particularly in human genomic DNA samples. When a sample is composed of an enormous number of sequences which are closely related to the specific target sequence, even the most unique probe sequence has a large number of partial hybridizations with non-target sequences.

The third problem relates to the unfavorable hybridization dynamics between a probe and its specific target.

Even under the best conditions, most hybridization reactions are conducted with relatively low concentrations of probes and target molecules. In addition, a probe often has to compete with the complementary strand for the target nucleic acid.

The fourth problem for most present hybridization formats is the high level of non-specific background signal. This is caused by the affinity of DNA probes to almost any material.

These problems, either individually or in combination, lead to a loss of sensitivity and/or specificity for nucleic acid hybridization in the above described formats. This is unfortunate because the detection of low copy number nucleic acid targets is necessary for most nucleic acid-based clinical diagnostic assays.

Because of the difficulty in detecting low copy number nucleic acid targets, the research community relies heavily on the polymerase chain reaction (PCR) for the amplification of target nucleic acid sequences (see M. A. Innis et al., *PCR Protocols: A Guide to Methods and Applications*, Academic Press, 1990). The enormous number of target nucleic acid sequences produced by the PCR reaction improves the subsequent direct nucleic acid probe techniques, albeit at the cost of a lengthy and cumbersome procedure.

A distinctive exception to the general difficulty in detecting low copy number target nucleic acid with a direct probe is the in-situ hybridization technique. This technique allows low copy number unique nucleic acid sequences to be detected in individual cells. In the in-situ format, target nucleic acid is naturally confined to the area of a cell ($\sim$20–50 $\mu m^2$) or a nucleus ($\sim$10 $\mu m^2$) at a relatively high local concentration. Furthermore, the probe/target hybridization signal is confined to a morphologically distinct area; this makes it easier to distinguish a positive signal from artificial or non-specific signals than hybridization on a solid support.

Mimicking the in-situ hybridization, new techniques are being developed for carrying out multiple sample nucleic acid hybridization analysis on micro-formatted multiplex or matrix devices (e.g., DNA chips) (see M. Barinaga, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application #570/87, 1987; R. Drmanac et al., 4 Genomics, 114, 1989; Strezoska et al., 88 Proc. Natl. Acad. Sci. USA 10089, 1991; and R. Drmanac and R. B. Crkvenjakov, U.S. Pat. No. 5,202,231, Apr. 13, 1993).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, United Kingdom Patent Application GB 8810400, 1988; E. M. Southern et al., 13 Genomics 1008, 1992, proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array.

Fodor et al., 364 Nature, pp. 555–556, 1993, used an array of 1,024 8-mer oligonucleotides on a solid support to sequence DNA. In this case, the target DNA was a fluorescently labeled single-stranded 12-mer oligonucleotide containing only nucleotides A and C. 1 pmol (~6×10$^{11}$ molecules) of the 12-mer target sequence was necessary for the hybridization with the 8-mer oLigomers on the array. The results showed many mismatches. Like Southern, Fodor et al., did not address the underlying problems of direct probe hybridization, such as stringency control for multiplex hybridizations. These problems, together with the requirement of a large quantity of the simple 12-mer target, indicate severe limitations to this SBH format.

Concurrently, Drmanac et al., 260 Science 1649–1652, 1993, used the second format to sequence several short (116 bp) DNA sequences. Target DNAs were attached to membrane supports ("dot blot" format). Each filter was sequentially hybridized with 272 labeled 10-mer and 11-mer oligonucleotides. A wide range of stringency condition was used to achieve specific hybridization for each n-mer probe; washing times varied from 5 minutes to overnight, and temperatures from 0° C. to 16° C. Most probes required 3 hours of washing at 16° C. The filters had to be exposed for 2 to 18 hours in order to detect hybridization signals. The overall false positive hybridization rate was 5% in spite of the simple target sequences, the reduced set of oligomer probes, and the use of the most stringent conditions available.

Fodor et al., 251 Science 767–773, 1991, used photolithographic techniques to synthesize oligonucleotides on a matrix. Pirrung et al., in U.S. Pat. No. 5,143,854, Sep. 1, 1992, teach large scale photolithographic solid phase synthesis of polypeptides in an array fashion on silicon substrates.

In another approach of matrix hybridization, Beattie et al., in *The* 1992 *San Diego Conference: Genetic Recognition*, November, 1992, used a microrobotic system to deposit micro-droplets containing specific DNA sequences into individual microfabricated sample wells on a glass substrate. The hybridization in each sample well is detected by interrogating miniature electrode test fixtures, which surround each individual microwell with an alternating current (AC) electric field.

Regardless of the format, current micro-scale DNA hybridization and SBH approaches do not overcome the underlying physical problems associated with direct probe hybridization reactions. They require very high levels of relatively short single-stranded target sequences or PCR amplified DNA, and produce a high level of false positive hybridization signals even under the most stringent conditions. In the case of multiplex formats using arrays of short oligonucleotide sequences, it is not possible to optimize the stringency condition for each individual sequence with any conventional approach because the arrays or devices used for these formats can not change or adjust the temperature, ionic strength, or denaturants at an individual location, relative to other locations. Therefore, a common stringency condition must be used for all the sequences on the device. This results in a large number of non-specific and partial hybridizations and severely limits the application of the device. The problem becomes more compounded as the number of different sequences on the array increases, and as the length of the sequences decreases. This is particularly troublesome for SBH, which requires a large number of short oligonucleotide probes.

Nucleic acids of different size charge, or conformation are routinely separated by electrophoresis techniques which can distinguish hybridization species by their differential mobility in an electric field. Pulse field electrophoresis uses an arrangement of multiple electrodes around a medium (e.g., a gel) to separate very large DNA fragments which cannot be resolved by conventional gel electrophoresis systems (see R. Anand and E. M. Southern in *Gel Electrophoresis of Nucleic Acids—A Practical Approach*, 2 ed., D. Rickwood and B. D. Hames Eds., IRL Press, New York, pp. 101–122, 1990).

Pace, U.S. Pat. No. 4,908,112, Mar. 13, 1990, teaches using micro-fabrication techniques to produce a capillary gel electrophoresis system on a silicon substrate. Multiple electrodes are incorporated into the system to move molecules through the separation medium within the device.

Soane and Soane, U.S. Pat. No. 5,126,022, Jun. 30, 1992, teach that a number of electrodes can be used to control the linear movement of charged molecules in a mixture through a gel separation medium contained in a tube. Electrodes have to be installed within the tube to control the movement and position of molecules in the separation medium.

Washizu, M. and Kurosawa, O., 26 IEEE Transactions on Industry Applications 6, pp. 1165–1172, 1990, used high-frequency alternating current (AC) fields to orient DNA molecules in electric field lines produced between microfabricated electrodes. However, the use of direct current (DC) fields is prohibitive for their work. Washizu 25 Journal of Electrostatic 109–123, 1990, describes the manipulation of cells and biological molecules using dielectrophoresis. Cells can be fused and biological molecules can be oriented along the electric fields lines produced by AC voltages between the micro-electrode structures. However, the dielectrophoresis process requires a very high frequency AC (1 MHz) voltage and a low conductivity medium. While these techniques can orient DNA molecules of different sizes along the AC field lines, they cannot distinguish between hybridization complexes of the same size.

As is apparent from the preceding discussion, numerous attempts have been made to provide effective techniques to conduct multi-step, multiplex molecular biological reactions. However, for the reasons stated above, these techniques have been proved deficient. Despite the long-recognized need for effective technique, no satisfactory solution has been proposed previously.

SUMMARY OF THE INVENTION

The present invention relates to the design, fabrication, and uses of a self-addressable self-assembling microelectronic system and device which can actively carry out controlled multi-step and multiplex reactions in microscopic formats. These reactions include, but are not limited to, most molecular biological procedures, such as nucleic acid hybridization, antibody/antigen reaction, and related clinical diagnostics. In addition, the device is able to carry out multi-step combinational biopolymer synthesis, including, but not limited to, the synthesis of different oligonucleotides or peptides at specific micro-locations.

The device is fabricated using both microlithographic and micro-machining techniques. The device has a matrix of addressable microscopic locations on its surface; each individual micro-location is able to electronically control and direct the transport and attachment of specific binding entities (e.g., nucleic acids, antibodies) to itself. All micro-locations can be addressed with their specific binding entities. Using this device, the system can be self-assembled with minimal outside intervention.

The device is able to control and actively carry out a variety of assays and reactions. Analytes or reactants can be transported by free field electrophoresis to any specific micro-location where the analytes or reactants are effectively concentrated and reacted with the specific binding entity at said micro-location. The sensitivity for detecting a specific analyte or reactant is improved because of the concentrating effect. Any un-bound analytes or reactants can be removed by reversing the polarity of a micro-location. Thus, the device also improves the specificity of assays and reactions.

The device provides independent stringency control for hybridization reactions at specific micro-locations. Thus all the micro-locations on the matrix can have different stringency conditions at the same time, allowing multiple hybridizations to be conducted at optimal conditions.

The device also facilitates the detection of hybridized complexes at each micro-location by using an associated optical (fluorescent or spectrophotometric) imaging detector system or an integrated sensing component.

In addition, the active nature of the device allows complex multi-step reactions to be carried out with minimal outside physical manipulations. If desired, a master device addressed with specific binding entities can be electronically replicated or copied to another base device.

Thus, the disclosed device can carry out multi-step and multiplex reactions with complete and precise electronic control, preferably with a micro-processor. The rate, specificity, and sensitivity of multi-step and multiplex reactions are greatly improved at specific micro-locations of the disclosed device.

The present invention overcomes the limitations of the arrays and devices for multi-sample hybridizations described in the background of the invention. Previous methods and devices are functionally passive regarding the actual hybridization process. While sophisticated photolithographic techniques were used to makes an array, or microelectronic sensing elements were incorporated for detection, previous devices did not control or influence the actual hybridization process. They are not designed to actively overcome any of the underlying physical problems associated with hybridization reactions.

This invention may utilize micro-locations of any size or shape consistent with the objective of the invention. In the preferred embodiment of the invention, micro-locations in the sub-millimeter range are used.

By "specific binding entity" is generally meant a biological or synthetic molecule that has specific affinity to another molecule, through covalent bonding or non-covalent bonding. Preferably, a specific binding entity contains (either by nature or by modification) a functional chemical group (primary amine, sulfhydryl, aldehyde, etc.), a common sequence (nucleic acids), an epitope (antibodies), a hapten, or a ligand, that allows it to covalently react or non-covalently bind to a common functional group on the surface of a micro-location. Specific binding entities include, but are not limited to: deoxyribonucleic acids (DNA), ribonucleic acids (RNA), synthetic oligonucleotides, antibodies, proteins, peptides, lectins, modified polysaccharides, synthetic composite macromolecules, functionalized nanostructures, synthetic polymers, modified/blocked nucleotides/nucleosides, modified/blocked amino acids, fluorophores, chromophores, ligands, chelates and haptens.

By "stringency control" is meant the ability to discriminate specific and non-specific binding interactions.

Thus, in a first aspect, the present invention features a device with an array of electronically self-addressable microscopic locations. Each microscopic location contains an underlying working direct current (DC) micro-electrode supported by a substrate. The surface of each micro-location has a permeation layer for the free transport of small counter-ions, and an attachment layer for the covalent coupling of specific binding entities.

By "array" or "matrix" is meant an arrangement of locations on the device. The locations can be arranged in two dimensional arrays, three dimensional arrays, or other matrix formats. The number of locations can range from several to at least hundreds of thousands.

In a second aspect, this invention features a method for transporting the binding entity to any specific micro-location on the device. When activated, a micro-location can affect the free field electrophoretic transport of any charged functionalized specific binding entity directly to itself. Upon contacting the specific micro-location, the functionalized specific binding entity immediately becomes covalently attached to the attachment layer surface of that specific micro-location. Other micro-locations can be simultaneously protected by maintaining them at the opposite potential to the charged molecules. The process can be rapidly repeated until all the micro-locations are addressed with their specific binding entities.

By "charged functionalized specific binding entity" is meant a specific binding entity that is chemically reactive (i.e., capable of covalent attachment to a location) and carrying a net change (either positive or negative).

In a third aspect, this inventions features a method for concentrating and reacting analytes or reactants at any specific micro-location on the device. After the attachment of the specific binding entities, the underlying micro-eletrode at each micro-location continues to function in a direct current (DC) mode. This unique feature allows relatively dilute charged analytes or reactant molecules free in solution to be rapidly transported, concentrated, and reacted in a serial or parallel manner at any specific micro-locations which are maintained at the opposite charge to the analyte or reactant molecules. Specific micro-locations can be protected or shielded by maintaining them at the same charge as the analytes or reactants molecules. This ability to concentrate dilute analyte or reactant. molecules at selected micro-locations greatly accelerates the reaction rates at these micro-locations.

When the desired reaction is complete, the micro-eletrode potential can be reversed to remove non-specific analytes or unreacted molecules from the micro-locations.

Specific analytes or reaction products may be released from any micro-location and transported to other locations for further analysis; or stored at other addressable locations; or removed completely from the system.

The subsequent analysis of the analytes at the specific micro-locations is also greatly improved by the ability to repulse non-specific entities from these locations.

In a fourth aspect, this invention features a method for improving stringency control of nucleic acid hybridization reactions, comprising the steps of:

rapidly concentrating dilute target DNA and/or probe DNA sequences at specific micro-location(s) where hybridization is to occur;

rapidly removing non-specifically bound target DNA sequences from specific micro-location(s) where hybridization has occurred;

rapidly removing competing complementary target DNA sequences from specific micro-location(s) where hybridization has occurred;

raising electric potential to remove partially hybridized DNA sequences (more than one base mis-match);

adjusting electric potential to improve the resolution of single mis-match hybridizations (e.g., to identify point mutations);

applying independent electric potential control to individual hybridization events occurring in the same bulk solution; and using electric potential control to improve hybridization of un-amplified target DNA sequences to arrays of capture oligonucleotide probes.

In a fifth aspect, this invention features a method for synthesizing biopolymers at micro-locations.

In a sixth aspect, this invention features a method for replicating a master device.

In a seventh aspect, this invention features methods for detecting and analyzing reactions that have occurred at the addressed micro-locations using self-addressed microelectronic devices with associated optical, optoelectronic or electronic detection systems or self-addressed microelectronic devices with integrated optical, optoelectronic or electronic detection systems.

BRIEF DESCRIPTION OF THE DRAWINGS

FIG. 1 is the cross-section of three self-addressable micro-locations fabricated using microlithographic techniques.

FIG. 2 is the cross-section of a microlithographically fabricated micro-location.

FIG. 3 is a schematic representation of a self-addressable 64 micro-location chip.

FIG. 4 shows particular attachment chemistry procedure which allows rapid covalent coupling of specific oligonucleotides to the attachment surface of a micro-location.

FIGS. 8a, 8b, 8c and 8d show the self-directed assembly of a device with three specific oligonucleotide binding entities (SSO-A, SSO-B, and SSO-C), FIG. 8a showing a first microlocation (ML-1) being addressed, FIG. 8b showing a second microlocation (ML-2) being addressed, FIG. 8c showing a third microlocation (ML-3) being addressed and FIG. 8d showing the three microlocations after being addressed and assembled.

FIGS. 13a, 13a and 13c show a scheme of electronically controlled replication of devices, FIG. 13a showing negatively charged addressable microlocations, FIG. 13a showing two opposed substrates, one substrate being that of FIG. 13a and the other being a sister device containing an attachment layer, and FIG. 13c showing two substrates, each of which has sequences bound to the microlocations.

DETAILED DESCRIPTION OF THE INVENTION

Figure 5:
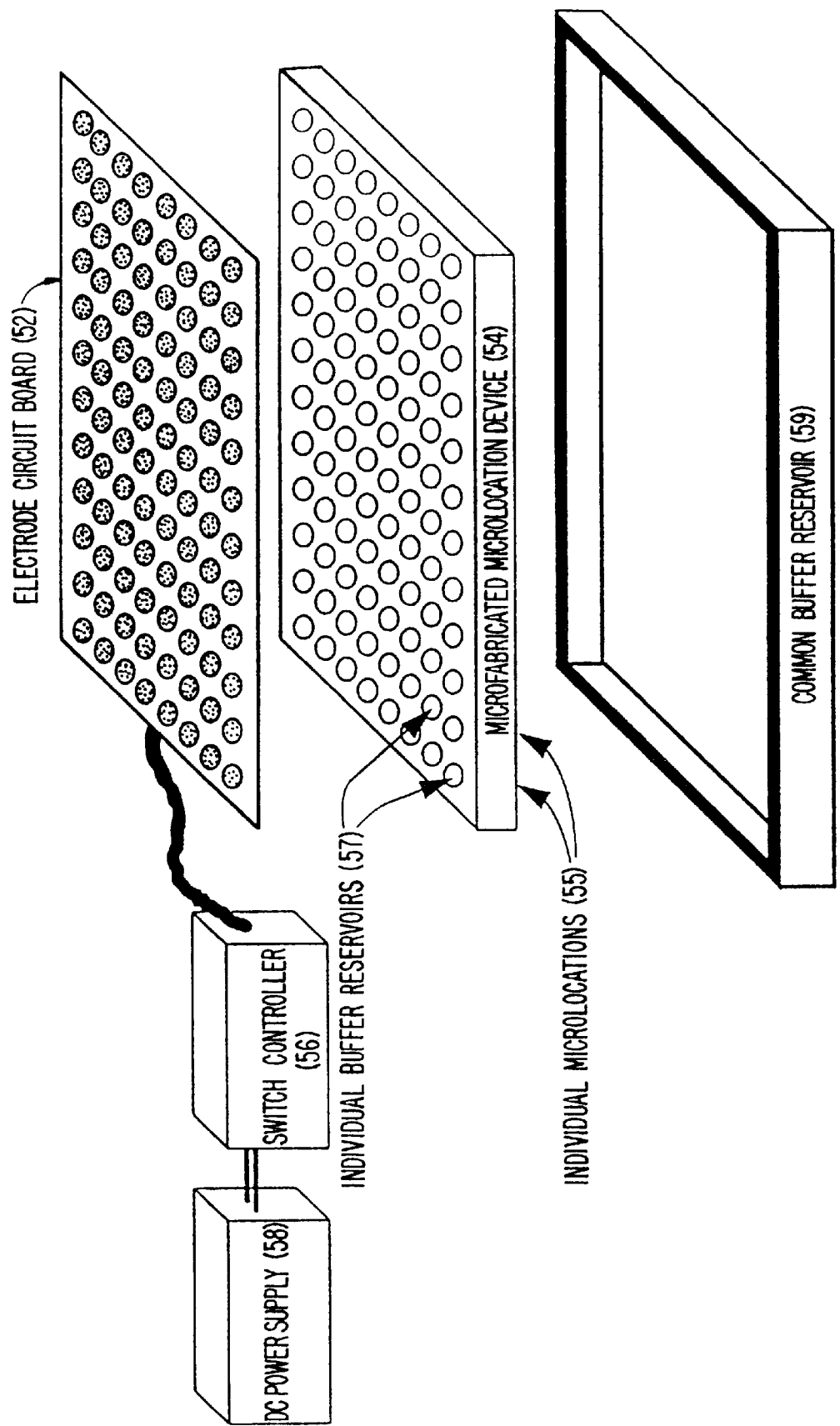
FIG. 5 is a blown-up schematic diagram of a micro-machined 96 micro-locations device.

The devices and the related methodologies of this invention allow important molecular biology and diagnostic reactions to be carried out under complete electronic control. The basic concept of this invention is a microelectronic device with specially designed addressable microscopic locations. Each micro-location has a derivatized surface for the covalent attachment of specific binding entities (i.e., an attachment layer), a permeation layer, and an underlying direct current (DC) micro-eletrode. After the initial fabrication of the basic microelectronic structure, the device is able to self-direct the addressing of each specific micro-location with specific binding entities. The self-addressed device is subsequently able to actively carry out multi-step, combinatorial, and multiplex reactions at any of its microlocations. The device is able tc electronically direct and control the rapid movement and concentration of analytes and reactants to or from any of its microlocations. The ability of the device to electronically control the dynamic aspects of various reactions provides a number of new and important advantages and improvements.

The concepts and embodiments of this invention are described in three sections. The first section, "Design and Fabrication of the Basic Devices," describes the design of the basic underlying microelectronic device and the fabrication of the device using microlithographic and micromachining techniques. The second section, "Self-Directed Addressing of the Devices," describes the self-addressing and self-assembly of the device, specifically the rapid transport and attachment of specific binding entities to each micro-location. The third section, "Applications of the Devices," describes how the device provides electronic control of various multi-step, combinatorial, and multiplex reactions. This section also describes the various uses and applications of the device.

(1) DESIGN AND FABRICATION OF THE BASIC DEVICES

In order for a device to carry out multi-step and multiplex reactions, its crucial electronic components must be able to maintain active operation in aqueous solutions. To satisfy this requirement, each microlocation must have an underlying functioning DC mode micro-electrode. Other considerations for the design and fabrication of a device include, but are not limited to, materials compatibilities, nature of the specific binding entities and the subsequent reactants and analytes, and the number of micro-locations.

By "a functioning DC mode micro-electrode" is meant a micro-electrode biased either positively or negatively, operating in a direct current mode (either continuous or pulse), which can affect or cause the free field electrophoretic transport of charged specific binding entities, reactants, or analytes to or from any location on the device, or in the sample solution.

Within the scope of this invention, the free field electrophoretic transport of molecules is not dependent on the electric field produced being bounded or confined by dielectrical material.

A device can be designed to have as few as two addressable micro-locations or as many as hundreds of thousands of micro-locations. In general, a complex device with a large number of micro-locations is fabricated using microlithography techniques. Fabrication is carried out on silicon or other suLtable substrate materials, such as glass, silicon dioxide, plastic, or ceramic materials. These microelectronic "chip" designs would be considered large scale array or multiplex analysis devices. A device with a small number of microlocations would be fabricated using micro-machining techniques.

Addressable micro-locations can be of any shape, preferably round, square, or rectangular. The size of an addressable micro-location can be of any size, preferably range from sub-micron (~0.5 $\mu$m) to several centimeters (cm) , with 5 $\mu$m to 100 $\mu$m being the most preferred size range for devices fabricated using microlithographic techniques, and 100 $\mu$m to 5 millimeters being the most preferred size range for devices fabricated using the micro-machining techniques. To make micro-locations smaller than the resolution of microlithographic methods would require techniques such as electron beam lithography, ion beam lithography, or molecular beam epitaxy. While microscopic locations are desirable for analytical and diagnostic type applications, larger addressable locations (e.g., larger than 2 mm) are desirable for preparative scale biopolymer synthesis.

After micro-locations have been created by using microlithographic and/or micro-machining techniques, chemical techniques are used to create the specialized attachment and permeation layers which would allow the DC mode micro-electrodes under the micro-locations to: (1) affect or cause the free field electrophoretic transport of specific (charged) binding entities from any location; (2) concentrate and covalently attach the specific binding entities to the specially modified surface of the specific micro-location; and (3) continue to actively function in the DC mode after the attachment of specific binding entities so that other reactants and analytes can be transported to or from the microlocations.

DESIGN PARAMETERS (MICROLITHOGRAPHY)

FIG. 1 shows a basic design of self-addressable microlocations fabricated using microlithographic techniques. The three micro-locations (10) (ML-1, ML-2, ML-3) are formed on the surface of metal sites (12) which have been deposited on an insulator layer/base material. The metal sites (12) serve as the underlying microeletrode structures (10). An insulator material separates the metal sites (12) from each other. Insulator materials include, but are not limited to, silicon dioxide, glass, resist, rubber, plastic, or ceramic materials.

FIG. 2 shows the basic features of an individual micro-location (10) formed on a microlithographically produced metal site (12). The addressable micro-location is formed on the metal site (12), and incorporates an oxidation layer (20), a permeation layer (22), an attachment layer (24), and a binding entity layer (26). The metal oxide layer provides a base for the covalent coupling of the permeation layer. The permeation layer provides spacing between the metal surface and the attachment/binding entity layers and allows solvent molecules, small counter-ions, and gases to freely pass to and from the metal surface. The thickness of the permeation layer for microlithographically produced devices can range from approximately 1 nanometers (nm) to 10 microns ($\mu$m), with 2 nm to 1 $\mu$m being the most preferred. The attachment layer provides a base for the covalent binding of the binding entities. The thickness of the attachment layer for microlithographically produced devices can range from 0.5 nm to 1 μm, with 1 nm to 200 nm being the most preferred. In some cases, the permeation and attachment layers can be formed from the same material. The specific binding entities are covalently coupled to the attachment layer, and form the specific binding entity layer. The specific binding entity layer is usually a mono-layer of the specific binding molecules. However, in some cases the binding entity layer can have several or even many layers of binding molecules.

Certain design and functional aspects of the permeation and attachment layer are dictated by the physical (e.g., size and shape) and the chemical properties of the specific binding entity molecules. They are also dictated to some extent by the physical and chemical properties of the reactant and analyte molecules, which will be subsequently transported and bound to the micro-location. For example, oligonucleotide binding entities can be attached to one type of micro-location surface without causing a loss of the DC mode function, i.e., the underlying micro-electrode can still cause the rapid free field electrophoretic transport of other analyte molecules to or from the surface to which the oligonucleotide binding entities are attached. However, if large globular protein binding entities (e.g., antibodies) are attached to the same type of surface, they may effectively insulate the surface and cause a decrease or a complete loss of the DC mode function. Appropriate modification of the attachment layer would have to be carried out so as to either reduce the number of large binding entities (e.g., large globular proteins) or provide spacing between the binding entities on the surface.

The spacing between micro-locations is determined by the ease of fabrication, the requirement for detector resolution between micro-locations, and the number of micro-locations desired on a device. However, particular spacings between micro-locations, or special arrangement or geometry of the micro-locations is not necessary for device function, in that any combination of micro-locations (i.e., underlying micro-electrodes) can operate over the complete device area. Nor is it necessary to enclose the device or confine the micro-locations with dielectric boundaries. This is because complex electronic field patterns or dielectric boundaries are not required to selectively move, separate, hold, or orient specific molecules in the space or medium between any of the electrodes. The device accomplishes this by attaching the specific binding molecules and subsequent analytes and reactants to the surface of an addressable micro-location.

Free field electrophoretic propulsion provides for the rapid and direct transport of any charged molecule between any and all locations on the device.

As the number of micro-locations increases beyond several hundred, the complexity of the underlying circuitry of the micro-locations increases. In this case the micro-location grouping patterns have to be changed and spacing distances increased proportionally, or multi-layer circuitry can be fabricated into the basic device.

In addition to micro-locations which have been addressed with specific binding entities, a device will contain some un-addressed, or plain micro-locations which serve other functions. These micro-locations can be used to store reagents, to temporarily hold reactants or analytes, and as disposal units for excess reactants, analytes, or other interfering components in samples. Other un-addressed micro-locations can be used in combination with the addressed micro-locations to affect or influence the reactions that are occurring at these specific micro-locations. These micro-locations add to intra-device activity and control. It is also possible for the micro-locations to interact and transport molecules between two separate devices. This provides a mechanism for loading a working device with binding entities or reactants from a storage device, and for copying or replicating a device.

FIG. 3 shows a matrix type device containing 64 addressable micro-locations (30). A 64 micro-location device is a convenient design, which fits with standard microelectronic chip packaging components. Such a device is fabricated on a silicon chip substrate approximately 1.5 cm×1.5 cm, with a central area approximately 750 μm×750 μm containing the 64 micro-locations. Each micro-location (32) is approximately 50 μm square with 50 μm spacing between neighboring micro-locations. Connective circuitry for each individual underlying micro-electrode runs to an outside perimeter (10 mm×10 mm) of metal contact pads (300 μm square) (34). A raised inner perimeter can be formed between the area with the micro-locations and the contact pads, producing a cavity which can hold approximately 2 to 10 microliters (μl) of a sample solution. The "chip" can be mounted in a standard quad package, and the chip contact pads (34) wired to the quad package pins. The packaged chip can then be plugged into a microprocessor controlled DC power supply and multimeter apparatus which can control and operate the device.

FABRICATION PROCEDURES (MICROLITHOGRAPHY)

Microlithography Fabrication Steps

General microlithographic or photolithographic techniques can be used for the fabrication of the complex "chip" type device which has a large number of small micro-locations. While the fabrication of devices does not require complex photolithography, the selection of materials and the requirement that an electronic device function actively in aqueous solutions does require special considerations.

The 64 micro-location device (30) shown in FIG. 3 can be fabricated using relatively simple mask design and standard microlithographic techniques. Generally, the base substrate material would be a 1 to 2 centimeter square silicon wafer or a chip approximately 0.5 millimeter in thickness. The silicon chip is first overcoated with a 1 to 2 μm thick silicon dioxide ($SiO_2$) insulation coat, which is applied by plasma enhanced chemical vapor deposition (PECVD).

In the next step, a 0.2 to 0.5 μm metal layer (e.g., aluminum) is deposited by vacuum evaporation. In addition to aluminum, suitable metals for circuitry include gold, silver, tin, copper, platinum, palladium, carbon, and various metal combinations. Special techniques for ensuring proper adhesion to the insulating substrate materials ($SiO_2$) are used with different metals.

The chip is next overcoated with a positive photoresist (Shipley, Microposit AZ 1350 J), masked (light field) with the circuitry pattern, exposed and developed. The photo-solubilized resist is removed, and the exposed aluminum is etched away. The resist island is now removed, leaving the aluminum circuitry pattern on the chip. This includes an outside perimeter of metal contact pads, the connective circuitry (wire), and the center array of micro-electrodes which serve as the underlying base for the addressable micro-locations.

Using PECVD, the chip is overcoated first with a 0.2 to 0.4 micron layer of $SiO_2$, and then with a 0.1 to 0.2 micron layer of silicon nitride ($Si_3N_4$). The chip is then covered with positive photoresist, masked for the contact pads and micro-electrode locations, exposed, and developed. Photosolubilized resist is removed, and the $SiO_2$ and $Si_3N_4$ layers are etched away to expose the aluminum contact pads and micro-electrodes. The surrounding island resist is then removed, the connective wiring between the contact pads and the micro-electrodes remains insulated by the $SiO_2$ and $Si_3N_4$ layers.

The $SiO_2$ and $Si_3N_4$ layers provide important properties for the functioning of the device. First, the second $SiO_2$ layer has better contact and improved sealing with the aluminum circuitry. It is also possible to use resist materials to insulate and seal. This prevents undermining of the circuitry due to electrolysis affects when the micro-electrodes are operating. The final surface layer coating of $Si_3N_4$ is used because it has much less reactivity with the subsequent reagents used to modify the micro-electrode surfaces for the attachment of specific binding entities.

Permeation and Attachment Layer Formation Steps

At this point the micro-electrode locations on the device are ready to be modified with a specialized permeation and attachment layer. This represents the most important aspect of the invention, and is crucial for the active functioning of the device. The objective is to create on the micro-electrode an intermediate permeation layer with selective diffusion properties and an attachment surface layer with optimal binding properties. The attachment layer should have from $10^5$ to $10^7$ functionalized locations per square micron ($\mu m^2$) for the optimal attachment of specific binding entities. However, the attachment of specific binding entities must not overcoat or insulate the surface so as to prevent the underlying micro-electrode from functioning. A functional device requires some fraction (~5% to 25%) of the actual metal micro-electrode surface to remain accessible to solvent ($H_2O$) molecules, and to allow the diffusion of counter-ions (e.g., $Na^+$ and $Cl^-$) and electrolysis gases (e.g., $O_2$ and $H_2$) to occur.

The intermediate permeation layer must also allow diffusion to occur. Additionally, the permeation layer should have a pore limit property which inhibits or impedes the larger binding entities, reactants, and analytes from physical contact with the micro-electrode surface. The permeation layer keeps the active micro-eletrode surface physically distinct from the binding entity layer of the micro-location.

In terms of the primary device function, this design allows the electrolysis reactions required for electrophoretic transport to occur on micro-electrode surface, but avoids adverse electrochemical effects to the binding entities, reactants, and analytes.

One preferred procedure for the derivatization of the metal micro-electrode surface uses aminopropyltriethoxy silane (APS). APS reacts readily with the oxide and/or hydroxyl groups on metal and silicon surfaces. APS provides a combined permeation layer and attachment layer, with primary amine groups for the subsequent covalent coupling of binding entities. In terms of surface binding sites, APS produces a relatively high level of functionalization (i.e., a large number of primary amine groups) on slightly oxidized aluminum surfaces, an intermediate level of functionalization on $SiO_2$ surfaces, and very limited functionalization of $Si_3N_4$ surfaces.

The APS reaction is carried out by treating the whole device (e.g., a chip) surface for 30 minutes with a 10% solution of APS in toluene at 50° C. The chip is then washed in toluene, ethanol, and then dried for one hour at 50° C. The micro-electrode metal surface is functionalized with a large number of primary amine groups ($10^5$ to $10^6$ per square micron). Binding entities can now be covalently bound to the derivatized micro-electrode urface.

The APS procedure works well for the attachment of oligonucleotide binding entities. FIG. 4 shows the mechanism for the attachment of 3'-terminal aldehyde derivatized oligonucleotides (40) to an APS functionalized surface (42). While this represents one of the preferred approaches, a variety of other attachment reactions are possible for both the covalent and non-covalent attachment of many types of binding entities.

DESIGN AND FABRICATION (MICRO-MACHINING)

This section describes how to use micro-machining techniques (e.g., drilling, milling, etc.) or non-lithographic techniques to fabricate devices. In general, these devices have relatively larger micro-locations (>100 microns) than those produced by microlithography.

These devices could be used for analytical applications, as well as for preparative type applications, such as biopolymer synthesis. Large addressable locations could be fabricated in three dimensional formats (e.g., tubes or cylinders) in order to carry a large amount of binding entities. Such devices could be fabricated using a variety of materials, including, but not limited to, plastic, rubber, silicon, glass (e.g., microchannelled, microcapillary, etc.), or ceramics. In the case of micro-machined devices, connective circuitry and larger electrode structures can be printed onto materials using standard circuit board printing techniques known to those skilled in the art.

Addressable micro-location devices can be fabricated relatively easily using micro-machining techniques.

FIG. 5 is a schematic of a representative 96 micro-location device. This micro-location device is fabricated from a suitable material stock (2 cm×4 cm×1 cm), by drilling 96 proportionately spaced holes (1 mm in diameter) through the material. An electrode circuit board (52) is formed on a thin sheet of plastic material stock, which fit precisely over the top of the micro-location component (54). The underside of the circuit board contains the individual wires (printed circuit) to each micro-location (55). Short platinum electrode structures (~3–4 mm) (62) are designed to extended down into the individual micro-location chambers (57). The printed circuit wiring is coated with a suitable water-proof insulating material. The printed circuit wiring converges to a socket, which allows connection to a multiplex switch controller (56) and DC power supply (58). The device is partially immersed and operates in a common buffer reservoir (59).

Figure 6:
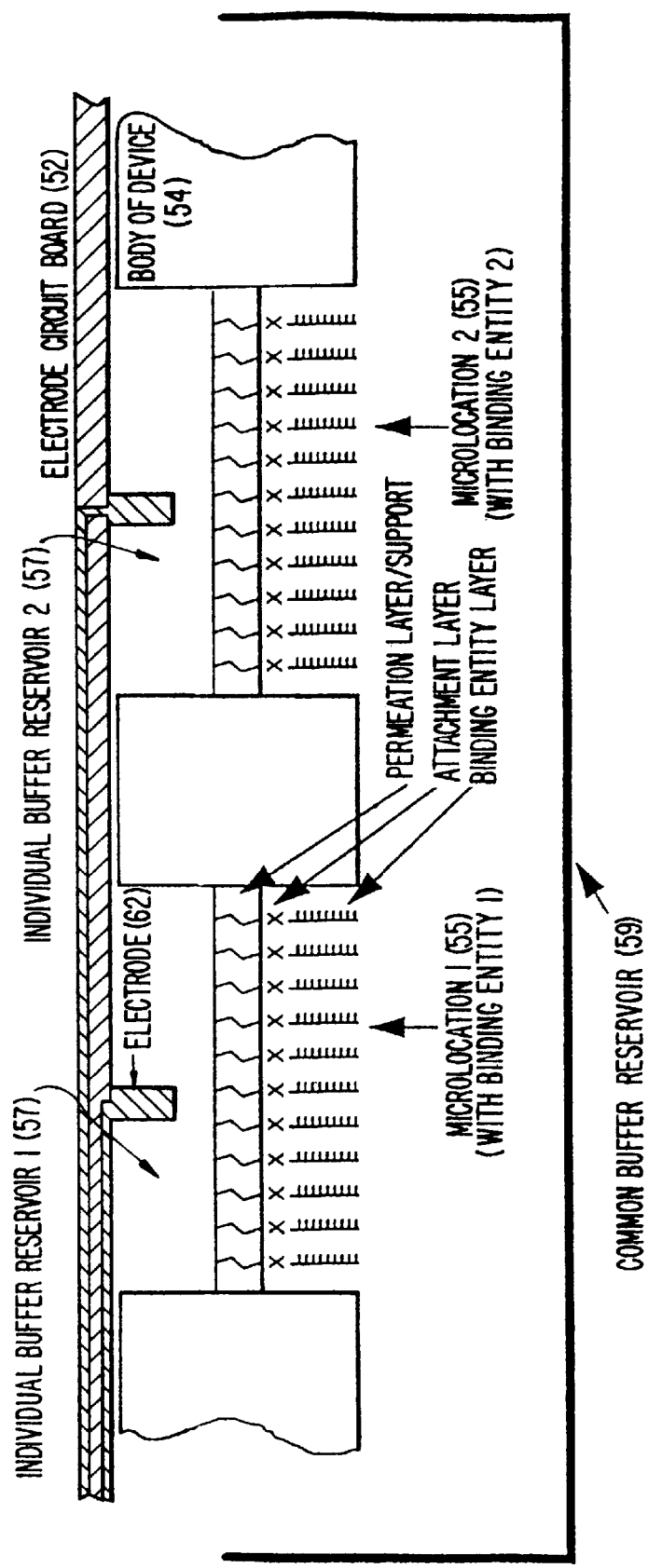
FIG. 6 is the cross-section of a micro-machined device.

While the primary function of the micro-locations in devices fabricated by micro-machining and microlithography techniques is the same, their designs are different. In devices fabricated by microlithography, the permeation and attachment layers are formed directly on the underlying metal micro-electrode. In devices fabricated by micro-machining techniques, the permeation and attachment layers are physically separated from their individual metal electrode structure (62) by a buffer solution in the individual chamber or reservoir (57) (see FIG. 6). In micro-machined devices the permeation and attachment layers can be formed using functionalized hydrophilic gels, membranes, or other suitable porous materials.

In general, the thickness of the combined permeation and attachment layers ranges from 10 $\mu$m to 10 mm. For example, a modified hydrophilic gel of 26% to 35% polyacrylamide (with 0.1% polylysine), can be used to partially fill (~0.5 mm) each of the individual micro-location chambers in the device. This concentration of gel forms an ideal permeation layer with a pore limit of from 2 nm to 3 nm. The polylysine incorporated into the gel provides primary amine functional groups for the subsequent attachment of specific binding entities. This type of gel permeation layer allows the electrodes to function actively in the DC mode. When the electrode is activated, the gel permeation layer allows small counter-ions to pass through it, but the larger specific binding entity molecules are concentrated on the outer surface. Here they become covalently bonded to the outer layer of primary amines, which effectively becomes the attachment layer.

An alternative technique for the formation of the permeation and attachment layers is to incorporate into the base of each micro-location chamber a porous membrane material. The outer surface of the membrane is then derivatized with chemical functional groups to form the attachment layer. Appropriate techniques and materials for carrying out this approach are known to those skilled in the art.

The above description for the design and fabrication of a device should not be considered as a limit to other variations or forms of the basic device. Many variations of the device with larger or smaller numbers of addressable micro-locations are envisioned for different analytical and preparative applications. variations of the device with larger addressable locations are envisioned for preparative biopolymer synthesis applications. Variations are also contemplated as electronically addressable and controllable reagent dispensers for use with other 30 devices, including those produced by microlithographic techniques.

(2) SELF-DIRECTED ADDRESSING OF THE DEVICES

The disclosed devices are able to electronically self-address each micro-location with a specific binding entity. The device itself directly affects or causes the transport and attachment of specific binding entities to specific micro-locations. The device self-assembles itself in the sense that no outside process, mechanism, or equipment is needed to physically direct, position, or place a specific binding entity at a specific micro-location. This self-addressing process is both rapid and specific, and can be carried out in either a serial or parallel manner.

Figure 7A:
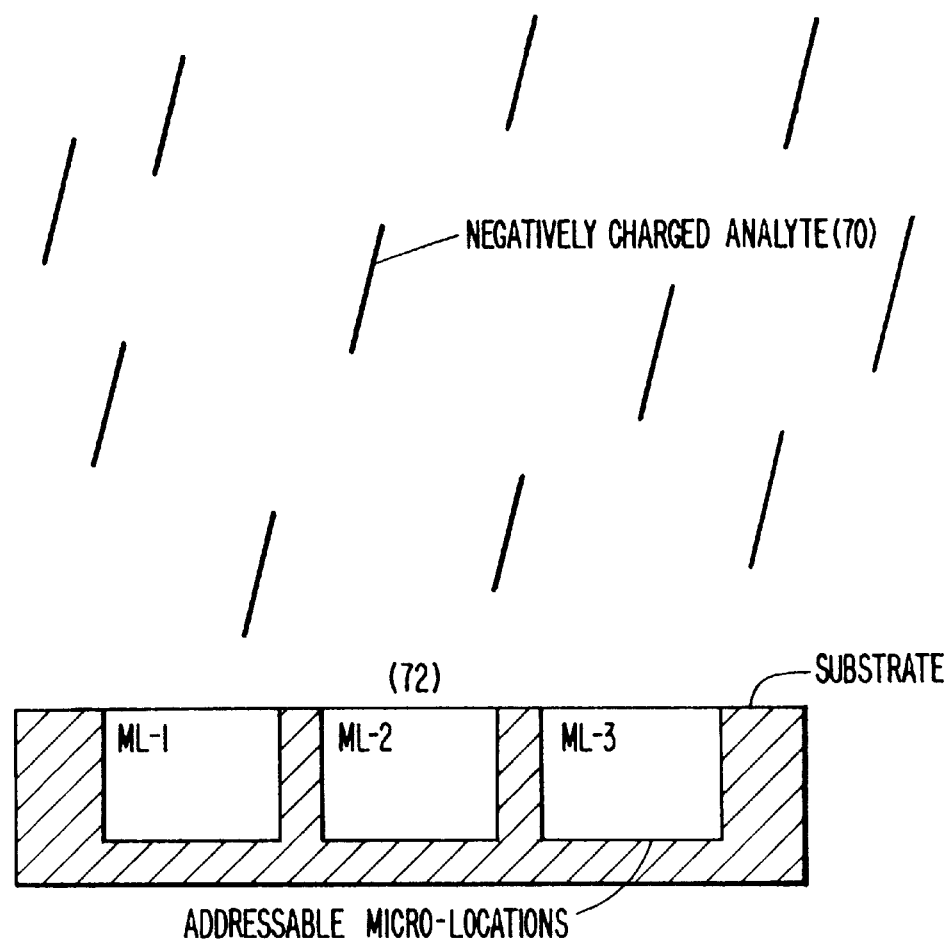
FIGS. 7a and FIG. 7b show the mechanism the device uses to electronically concentrate analyte or reactant molecules at a specific micro-location, FIG. 7a showing the addressable microlocations in a neutral condition and FIG. 7b showing the addressable microlocations in a charged state.
Figure 7B:
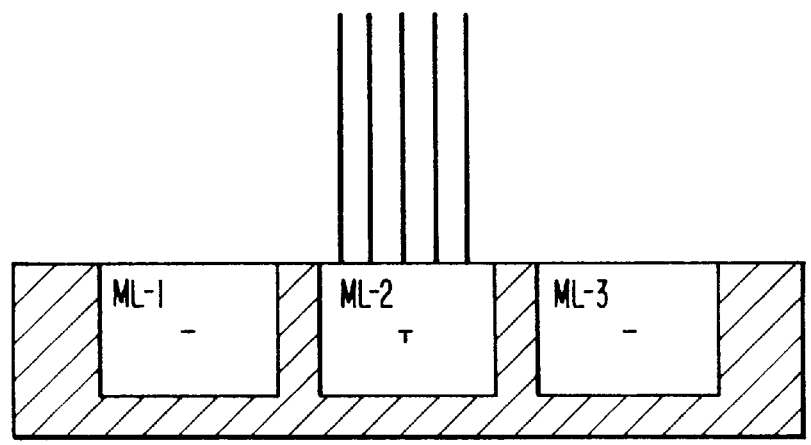

A device can be serially addressed with specific binding entities by maintaining the selected micro-location in a DC mode and at the opposite charge (potential) to that of a specific binding entity. All other micro-locations are maintained at the same charge as the specific binding entity. In cases where the binding entity is not in excess of the attachment sites on the micro-location, it is necessary to activate only one other micro-electrode to affect the electrophoretic transport to the specific micro-location. The specific binding entity is rapidly transported (in a few seconds, or preferably less than a second) through the solution, and concentrated directly at the specific micro-location where it immediately becomes covalently bonded to the special surface. The ability to electronically concentrate reactants or analytes (70) on a specific micro-location (72) is shown in FIGS. 7a and 7b. All other micro-locations remain unaffected by that specific binding entity. Any unreacted binding entity is removed by reversing the polarity of that specific micro-location, and electrophoresing it to a disposal location. The cycle is 30 repeated until all desired micro-locations are addressed with their specific binding entities. FIGS. 8a through 8d shows the serial process for addressing specific micro-locations (81, 83, 85) with specific oligonucleotide binding entities (82, 84, 86).

The parallel process for addressing micro-locations simply involves simultaneously activating a large number (particular group or line) of micro-electrodes so that the same specific binding entity is transported, concentrated, and reacted with more than one specific micro-locations.

(3) APPLICATIONS OF THE DEVICES

Once a device has been self-addressed with specific binding entities, a variety of molecular biology type multistep and multiplex reactions and analyses can be carried out on the device. The devices of this invention are able to electronically provide active or dynamic control over a number of important reaction parameters.

This electronic control leads to significant improvements in reaction rates, specificities, and sensitivities. The improvements in these reaction parameters come from the ability of the device to electronically control and affect: (1) the rapid transport of reactants or analytes to a specific micro-location containing attached specific binding entities; (2) improvement in reaction rates due to the concentrated reactants or analytes reacting with the specific binding entities at that specific micro-location; and (3) the rapid and selective removal of un-reacted and non-specifically bound components from that micro-location. These advantages are utilized in a novel process called "electronic stringency control".

The self-addressed devices of this invention are able to rapidly carry out a variety of micro-formatted multistep and/or multiplex reactions and procedures; which include, but are not limited to:

DNA and RNA hybridizations procedures and analysis in conventional formats, and new improved matrix formats;

molecular biology reaction procedures, e.g., restriction enzyme reactions and analysis, ligase reactions, kinasing reactions, and amplification procedures;

antibody/antigen reaction procedures involving large or small antigens and haptens;

diagnostic assays, e.g., hybridization analysis, gene analysis, fingerprinting, and immunodiagnostics;

biomolecular conjugation procedures (i.e. the covalent and non-covalent labeling of nucleic acids, enzymes, proteins, or antibodies with reporter groups);

biopolymer synthesis procedures, e.g., combinatorial synthesis of oligonucleotides or peptides;

water soluble synthetic polymer synthesis, e.g., carbohydrates or linear polyacrylates; and macromolecular and nanostructure (nanometer size particles and structures) synthesis and fabrication.

NUCLEIC ACID HYBRIDIZATION

Nucleic acid hybridizations are used as examples of this invention because they characterize the most difficult multistep and multiplex reactions.

The disclosed device and methods allow nucleic acid hybridization to be carried out in a variety of conventional and new formats. The ability of the device to electronically control reaction parameters greatly improves nucleic acid hybridization analysis, particularly the ability of the device to provide electronic stringency control (ESC).

By "nucleic acid hybridization" is meant hybridization between all natural and synthetic forms and derivatives of nucleic acids, including: deoxyribonucleic acid (DNA), ribonucleic acid (RNA), polynucleotides and oligonucleotides.

Conventional hybridization formats, such as "dot blot" hybridization and "sandwich" hybridization, can be carried out with the disclosed device as well as large scale array or matrix formats.

As an example, a device for DNA hybridization analysis is designed, fabricated, and used in the following manner. Arrays of micro-locations are first fabricated using microlithographic techniques. The number of addressable micro-locations on an array depends on the final use. The device is rapidly self-addressed in a serial manner with a group of specific oligonucleotides. In this case, the specific oligonucleotides are 3'-terminal aldehyde functionalized oligonucleotides (in the range of 6-mer to 100-mer). The aldehyde functional group allows for covalent attachment to the specific micro-location attachment surface (see FIG. 4). This group of specific oligonucleotides can be readily, synthesized on a conventional DNA synthesizer using conventional techniques.

The synthesis of each specific oligonucleotide is initiated from a ribonucleotide controlled pore glass (CPG) support. Thus, the 3'-terminal position contains a ribonucleotide, which is then easily converted after synthesis and purification to a terminal dialdehyde derivative by periodate oxidation. The aldehyde containing oligonucleotides (40) will react readily with the primary amine functional groups on the surface of micro-locations by a Schiff's base reaction process.

The electronic addressing of the device with specific oligonucleotides is shown in FIGS. 8a through 8d. The addressing of the first specific micro-location (Ml-1) (81) with its specific sequence oligonucleotide (SSC)-1) (82) is accomplished by maintaining the specific microelectrode (ML-1) at a positive DC potential, while all other microeletrodes are maintained at a negative potential (FIG. 8(A)). The aldehyde functionalized specific sequence (SSO-1) in aqueous buffered solution is free field electrophoresed to the ML-1 address, where it concentrates (>$10^6$ fold) and immediately becomes covalently bound to the surface of ML-1 (81). All other micro-eletrodes are maintained negative, and remain protected or shielded from reacting with SSO-1 sequence (82). The ML-1 potential is then reversed to negative (−) to electrophores any unreacted SSO-1 to a disposal system. The cycle is repeated, SSO-2 (84)→ML-2 (83), SSO-3 (86)→ML-3 (85), SSO-n→ML-n until all the desired micro-locations are addressed with their specific DNA sequences (FIG. 8(D)).

Another method for addressing the device is to transport specific binding entities such as specific oligonucleotides from an electronic reagent supply device. This supply device would hold a large quantity of binding entities or reagents and would be used to load analytical devices. Binding entities would be electronically transported between the two devices. Such a process eliminates the need for physical manipulations, such as pipetting, in addressing a device with binding entities.

Yet another method for addressing the device is to carry out the combinatorial synthesis of the specific oligonucleotides at the specific micro-locations. Combinatorial synthesis is described in a later section.

After the device is addressed with specific DNA sequences, the micro-locations on the array device remain an independent working direct current (DC) electrodes. This is possible because the attachment to the electrode surface is carried out in such a manner that the underlying microelectrode does not become chemically or physically insulated. Each micro-electrode can still produce the strong direct currents necessary for the free field electrophoretic transport of other charged DNA molecules to and from the micro-location surface. The DNA array device provides complete electronic control over all aspects of the DNA hybridization and any other subsequent reactions.

Figure 9A:
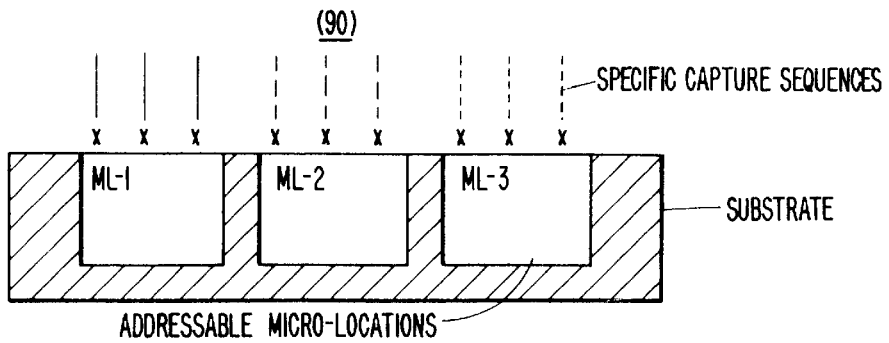
FIGS. 9a, 9b and 9c show an electronicaLly controlled hybridization process with sample/target DNA being concentrated at micro-locations containing specific DNA capture sequences, FIG. 9a showing specific capture sequences on addressable microlocations, FIG. 9b showing specific and nonspecific DNA adjacent the structure of FIG. 9a, and FIG. 9c showing hybridized material adjacent microlocations ML-1 and ML-3.
Figure 9B:
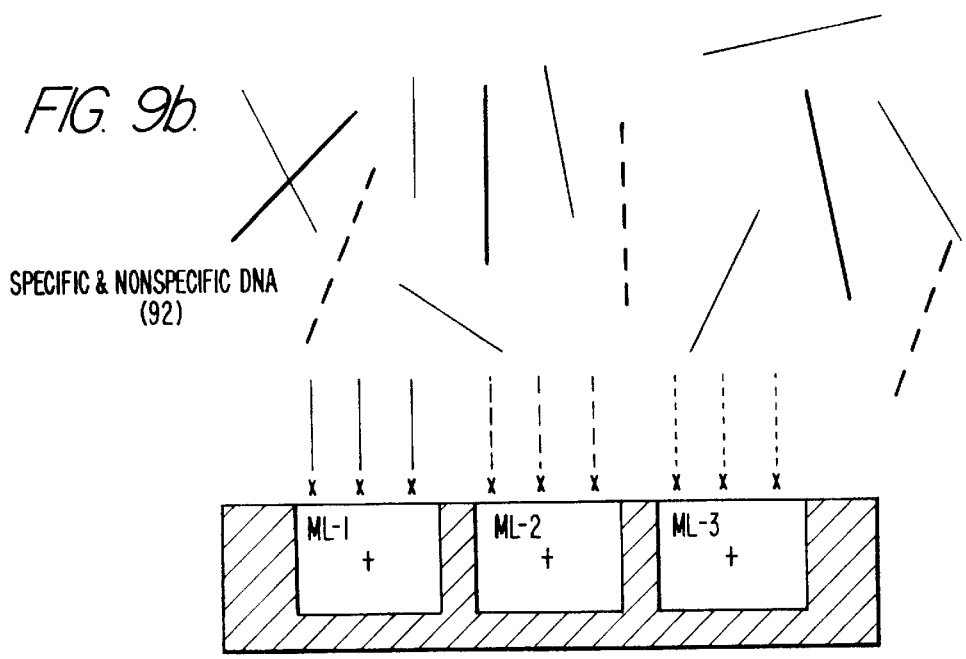
Figure 9C:
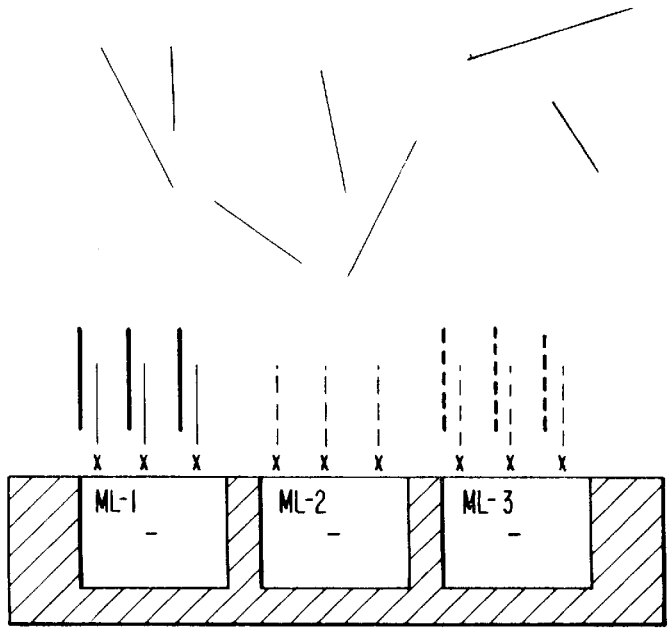

An example of an electronically controlled hybridization process is shown in FIGS. 9a through 9c. In this case, each addressable micro-location has a specific capture sequence (90). A sample solution containing target DNA (92) is applied to the device. All the micro-locations are activated and the sample DNA is concentrated at the micro-locations (FIG. 9(B)). Target DNA molecules from the dilute solution become highly concentrated at the micro-locations, allowing very rapid hybridization to the specific complementary DNA sequences on the surface. Reversal of the micro-electrode potential repels all unhybridized DNA from the micro-locations, while the target DNA remains hybridized (FIG. 9(C)). In similar fashion, reporter probes are hybridized in subsequent steps to detect hybridized complexes.

The electronic control of the hybridization process significantly improves the subsequent detection of the target DNA molecules by enhancing the overall hybridization efficiency and by removing non-specific DNA from the micro-location areas. It is expected that 10,000 to 100,000 copies of target sequences in un-amplified genomic DNA will be detectable. Hybridization reactions of this type can be carried out in a matter of minutes, with minimal outside manipulations. Extensive washing is not necessary.

Figure 10A:
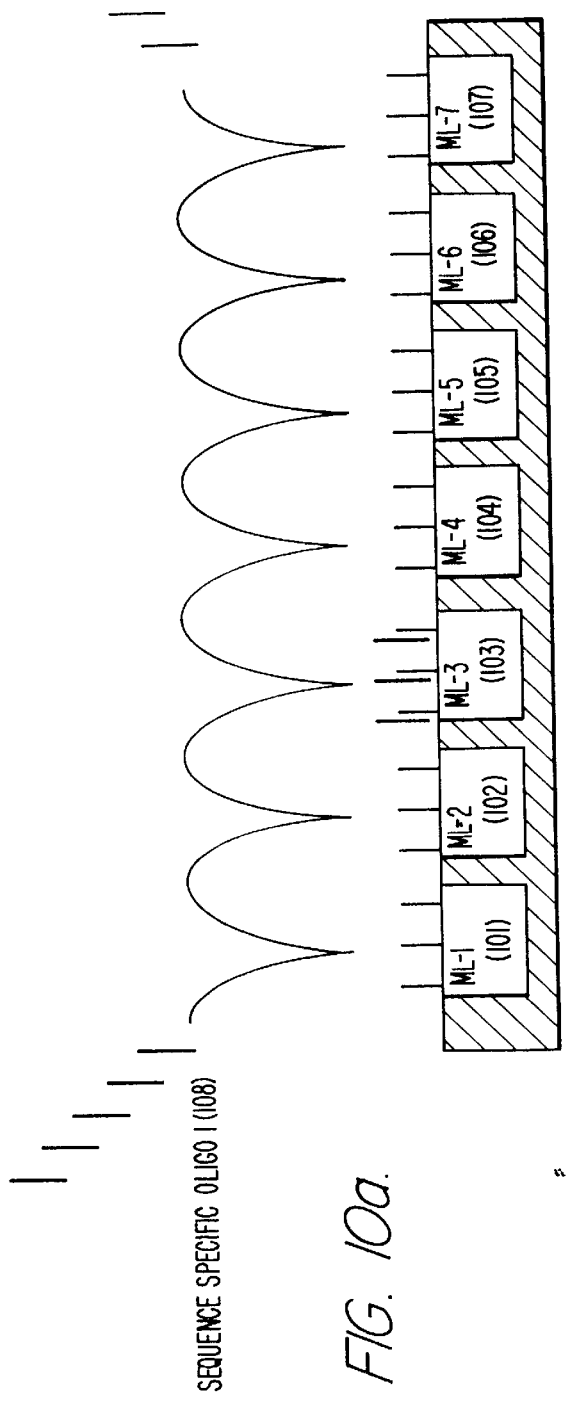
FIGS. 10a and 10b show an electronically directed serial hybridization process, FIG. 10a showing materials adjacent microlocation ML-3 and FIG. 10b showing materials adjacent microlocations ML-3 and ML-5.
Figure 10B:
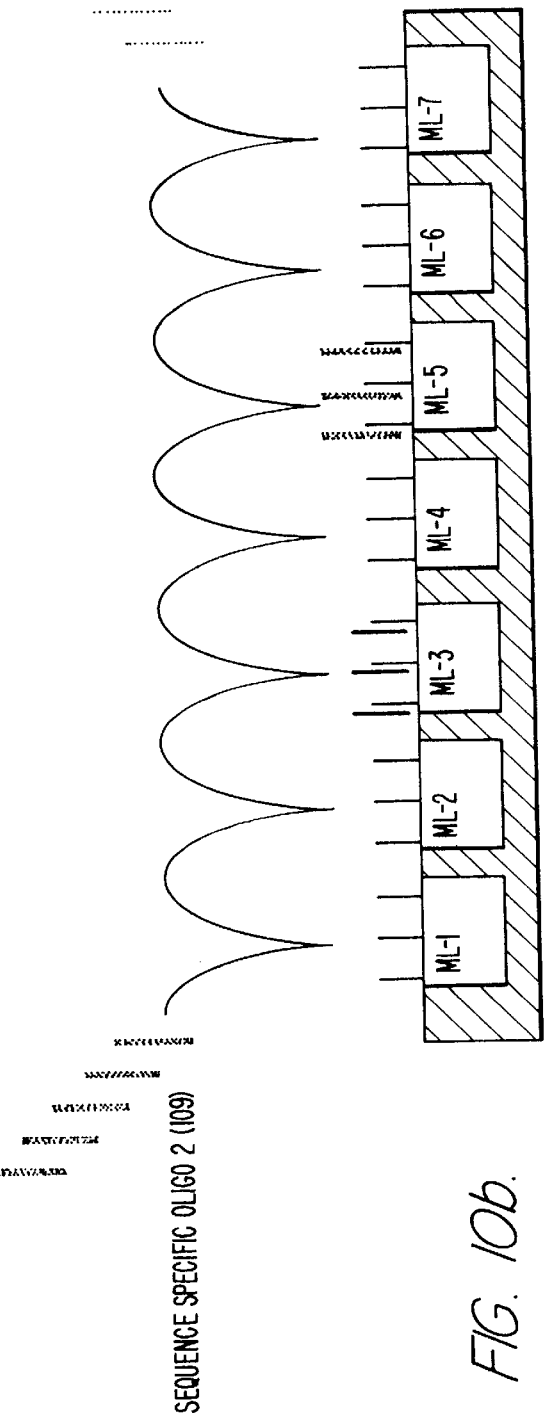

Another common format for DNA hybridization assays involves having target DNAs immobilize on a surface, and then hybridizing specific probes to these target DNAs. This format can involve either the same target DNAs at multiple locations, or different target DNAs at specific locations. FIGS. 10a and 10b shows an improved version of this serial hybridization format. In this case micro-locations (101–107) are addressed with different capture DNAs. These are hybridized in a serial fashion with different sequence specific oligonucleotides (108,109). The micro-locations are sequentially biased positive to transport molecules to itself and then biased negative to transport molecules to the next micro-location. Specifically hybridized DNA will remain at the micro-location regardless of electrode potential. The sequence specific oligonucleotides can be labeled with a suitable reporter group such as a fluorophore.

Figure 11A:
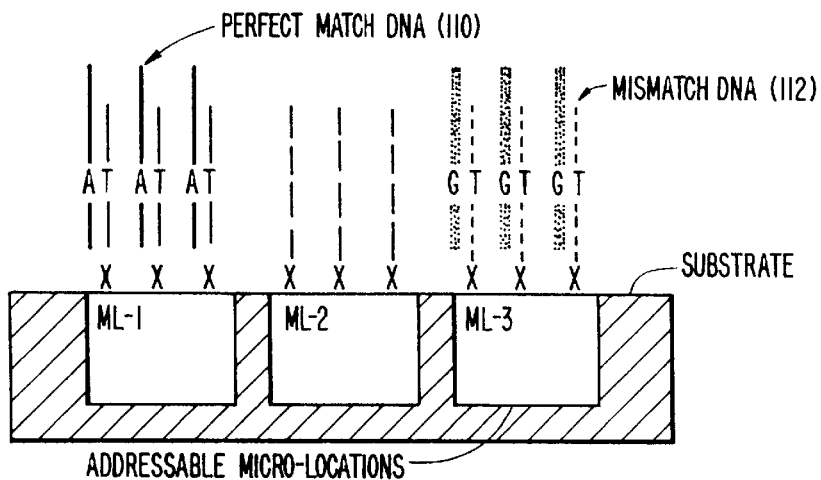
FIGS. 11a, 11b and 11c show the electronic stringency control (ESC) of a hybridization process for determining single point mutations, FIG. 11a showing uncharged addressable microlocations, FIG. 11b showing negatively charged microlocations and FIG. 11c showing negatively charged microlocations with material denatured from microlocation ML-3.
Figure 11B:
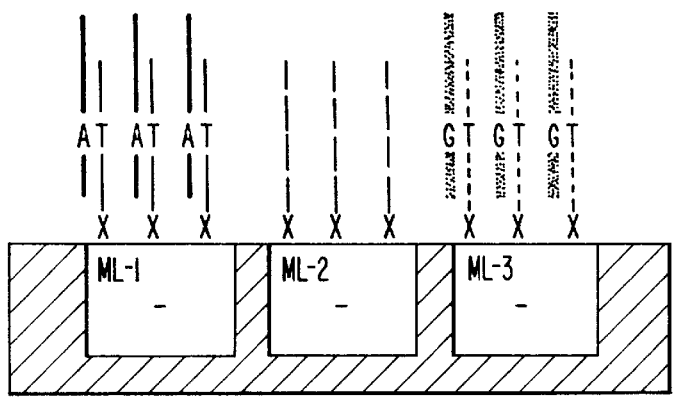
Figure 11C:
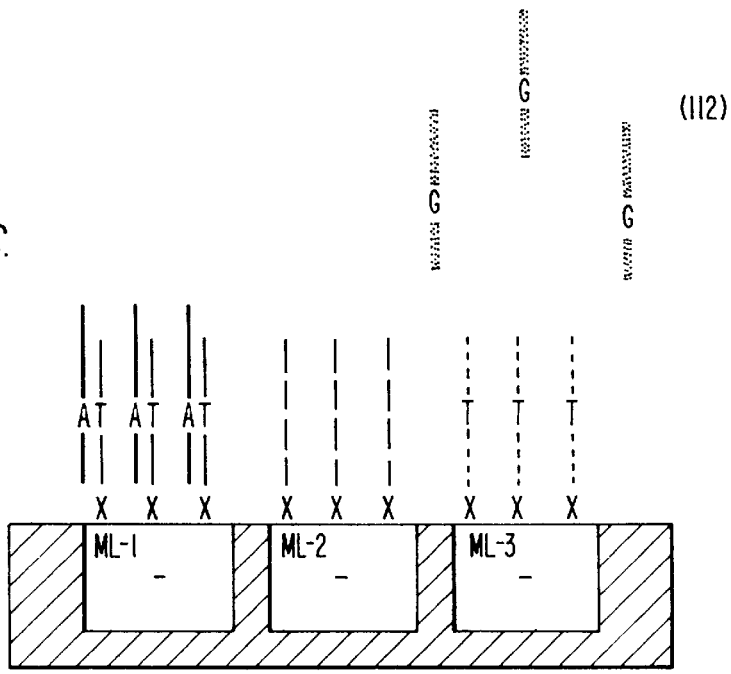

The disclosed device is able to provide electronic stringency control. Stringency control is necessary for hybridization specificity, and is particularly important for resolving one base mismatches in point mutations. FIGS. 11a through 11c shows how electronic stringency control can be used for improving hybridization specificity for one base mismatch analysis. The electronic stringency control can also be applied to multiple-base mismatch analysis.

Perfectly matched DNA hybrids (110) are more stable than mismatched DNA (112) hybrids. By biasing the microlocations negative (FIG. 11(B)) and delivering a defined amount of power in a given time, it is possible to denature or remove the mismatched DNA hybrids while retaining the perfectly matched DNA hybrids (FIG. 11(C)). In a further refinement, the disclosed device provides independent stringency control to each specific hybridization reaction occurring on the device. With a conventional or passive array format, it is impossible to achieve optimal stringency for all the hybridization events which are occurring in the same hybridization solution. However, the active array devices of this invention are able to provide different electronic stringency, to hybridizations at different micro-locations, even though they are occurring in the same bulk hybridization solution. This attribute overcomes a major limitation to conventional matrix hybridization formats, sequencing by hybridization (SBH) formats, and other multiplex analyses.

Figure 12A:
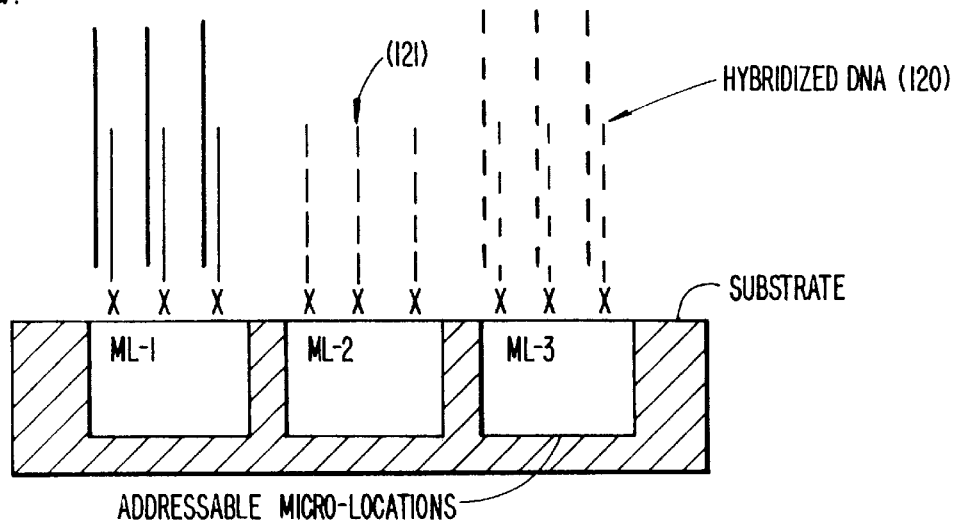
FIGS. 12a, 12b, 12c and 12d show a scheme for the detection of hybridized DNA without using labeled DNA probe, i.e., electronically controlled fluorescent dye detection process, FIG. 12a showing uncharged microlocations, FIG. 12b showing negatively charged microlocations, FIG. 12c showing uncharged microlocations with dye and FIG. 12d showing positively charged microlocations.
Figure 12B:
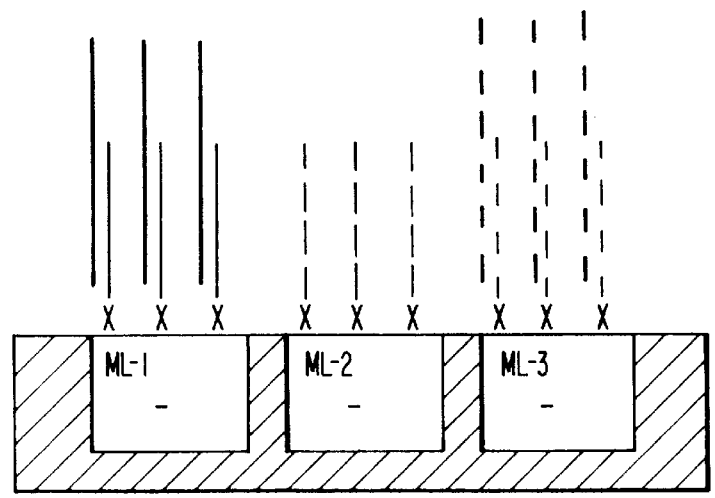
Figure 12C:
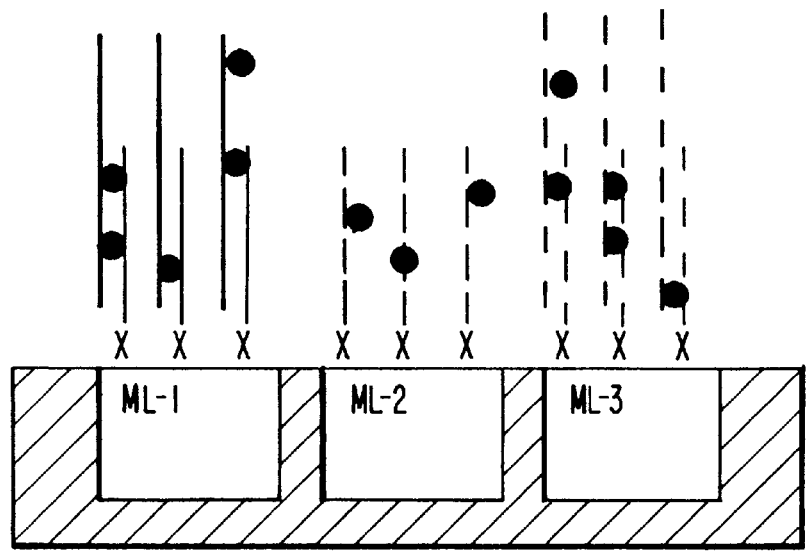
Figure 12D:
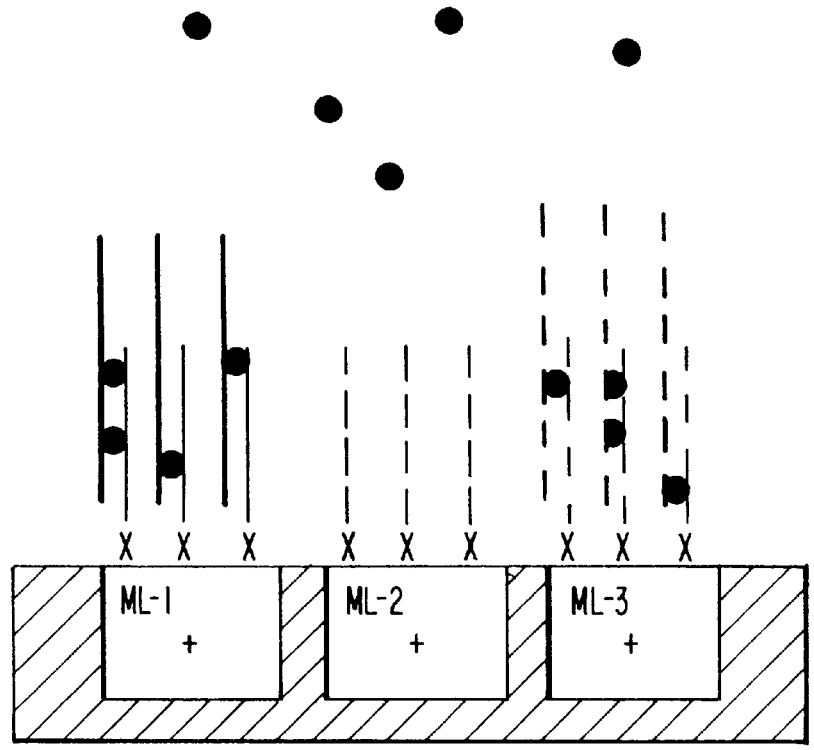

The ability to provide electronic stringency control to hybridizations also provides mechanisms for detecting DNA hybridization without reporter group labeled DNA probe. It provides a way to carry out a more direct detection of the hybridization process itself. A fluorescent dye detection process is shown in FIGS. 12a through 12d and described in Examples 4 and 6. Direct detection of DNA hybrids can be achieved by using DNA binding dyes such as ethidium bromide. The dye binds to both double-stranded and single-stranded DNA but with a greater affinity for the former. In FIG. 12(B) positively charged dye (122) is transported to negatively biased micro-locations. The dye binds to both hybridized (120) and unhybridized (121) DNA sequences (FIG. 12c). By biasing the micro-locations positive and delivering a defined amount of power in a given amount of time, the dye molecules bound to unhybridized micro-locations is selectively removed. The amount of power applied does not adversely affect the DNA hybrids.

The hybridized DNAs with associated dye molecules are then fluorescently detected using associated or integrated optical systems.

The following reiterates the important advantages the devices of this invention provide for nucleic acid hybridization reactions and analysis:

(1) The rapid transport of dilute target DNA and/or probe DNA sequences to specific micro-location(s) where hybridization is to occur. This process takes place in no more than a few seconds.

(2) Concentrating dilute target DNA and/or probe DNA sequences at specific micro-location(s) where hybridization is to occur. The concentrating effect can be well over a million fold ($>10^6$)

(3) The rapid removal of non-specifically bound target DNA sequences from specific micro-location(s) where hybridization has occurred. This process takes 10 to 20 seconds.

(4) Rapid removal of competing complementary target DNA sequences from specific micro-location(s) where hybridization has occurred. This process takes 10 to 20 seconds.

(6) The ability to carry out a complete hybridization process in several minutes.

(7) The ability to carry out a hybridization process with minimal outside manipulations or washing steps.

(8) The use of electronic stringency control (ESC) to remove partially hybridized DNA sequences.

(9) The ability to carry out hybridization analysis of un-amplified genomic target DNA sequences in the 1000 to 100,000 copy range.

(10) The use of ESC to improve the resolution of single base mis-match hybridizations (point mutations).

(11) The use of ESC to provide individual stringency control in matrix hybridizations.

(12) Improving the detection of hybridization event by removing non-specific background components.

(13) The development of new procedures which eliminate the need for using covalently labeled reporter probes or target DNA to detect the hybridization events.

REPRODUCTION OF DEVICES

Figure 13C:
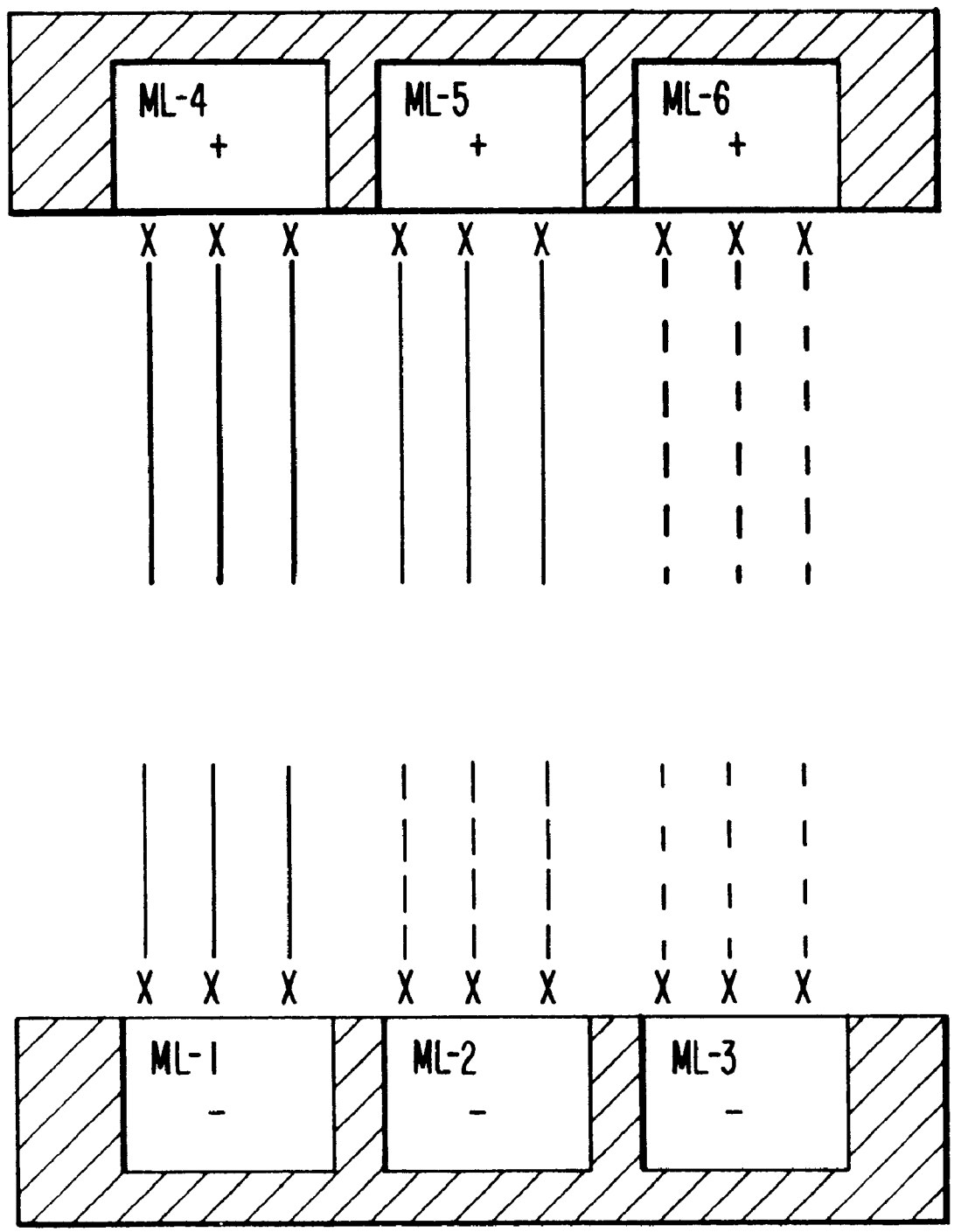

In addition to separately addressing individual devices with specific binding entities, it is also possible to produce a master device, which can copy specific binding entities to other devices. This represents another method for the production of devices. The process for the replication of devices is shown in FIGS. 13a through 13c. A master device containing micro-locations which have been addressed with specific binding sequences is hybridized with respective complementary DNA sequences (130). These complementary sequences are activated and thus capable of covalent binding to the micro-location attachment layer.

An unaddressed sister device (132) containing an attachment layer is aligned with the hybridized master device (FIG. 13(B)). The master device micro-locations are biased negative and the sister device micro-locations are biased positive. The DNA hybrids are denatured and are transported to the sister device, where the activated DNA sequence binds covalently to the micro-location (FIG. 13(C)). The process can be performed in parallel or in series, depending on the device geometry so that crosstalk between the micro-locations is minimized. The hybrids can be denatured by applying a sufficient negative potential or by using a positively charged chaotropic agent or denaturant.

DETECTION SYSTEM

In the case of fluorescent binding reactions, it is possible to use an epifluorescent type microscopic detection system for the analysis of the binding reactions. The sensitivity of the system depends on the associated imaging detector element (CCD, ICCD, Microchannel Plate) or photon counting PMT system. One alternative is to associate a sensitive CCD detector or avalanche photodiode (APD) detector directly with the device in a sandwich arrangement. Another alternative is to integrate optoelectronic or microelectronics detection in the device.

COMBINATORIAL BIOPOLYMER SYNTHESIS

The devices of this invention are also capable of carrying out combinatorial synthesis of biopolymers such as oligonucleotides and peptides. Such a process allows self-directed synthesis to occur without the need for any outside direction or influence. This combinatorial synthesis allows very large numbers o: sequences to be synthesized on a device. The basic concept for combinatorial synthesis involves the use of the device to transport, concentrate, and react monomers, coupling reagents, or deblocking reagents at the addressable micro-locations. The concept capitalizes on the ability of the device to protect certain locations from the effects of nearby reagents. Also important to the concept is the identification of selective steps in these chemical synthesis processes where one or more of the reactants has either a net positive or negative charge, or to create such suitable reagents for these processes.

One method for combinatorial oligonucleotide synthesis is shown in FIGS. 14a through 14f. This method begins with a set of selectively addressable micro-locations (140) whose surfaces have been derivatized with blocked primary amine (X—NH—) groups (142). The initial step in the process involves selective deblocking of electrodes using a charged deblocking reagent (144). In this case, the reagent would carry a positive (+) charge. The process is carried out by applying a negative potential to those electrodes being de-blocked, and a positive potential to those which are to remain protected (FIG. 14(B)). Application of positive and negative potentials to selective electrodes causes the charged reagents to be concentrated at those micro-locations being de-blocked, and excludes the reagents from the other electrode surfaces.

In the second step, chemical coupling of the first base, in this case cytosine, to the deblocked micro-locations is carried out by simply exposing the system to 30 the phosphoramidite reagent (x-C) (146). The (C) nucleotide couples to de-blocked micro-location surfaces, but not to any of the blocked electrode surfaces (FIG. 14(C) and (D)). At this point normal phosphoramide chemistry is carried out until the next de-blocking step.

Figure 14A:
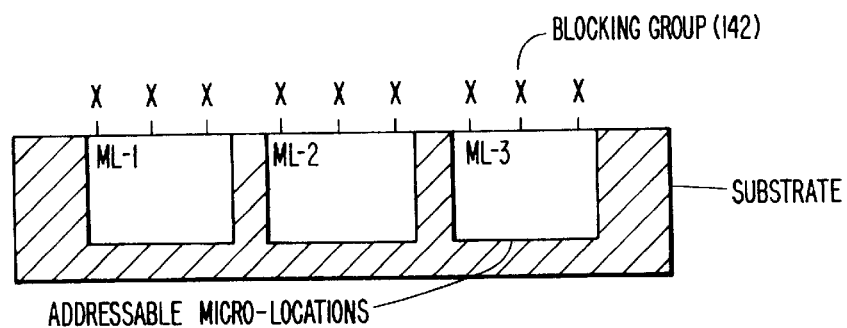
FIGS. 14a, 14b, 14c, 14d, 14e, and 14f show a scheme of electronically directed combinatorial synthesis of oligonucleotides, FIG. 14a showing addressable microlocations with blocking groups, FIG. 14b showing addressable microlocations with blocking groups in combination with a deblocking group, FIG. 14c showing blocked and deblocked addressable microlocations in the presence of monomer C, FIG. 14d showing addressable microlocations in combination with a deblocking group, FIG. 14e showing deblocked cites on microlocation ML-2 in the presence of monomer A and FIG. 14f showing microlocations with blocking groups on the terminal ends of sequences.
Figure 14B:
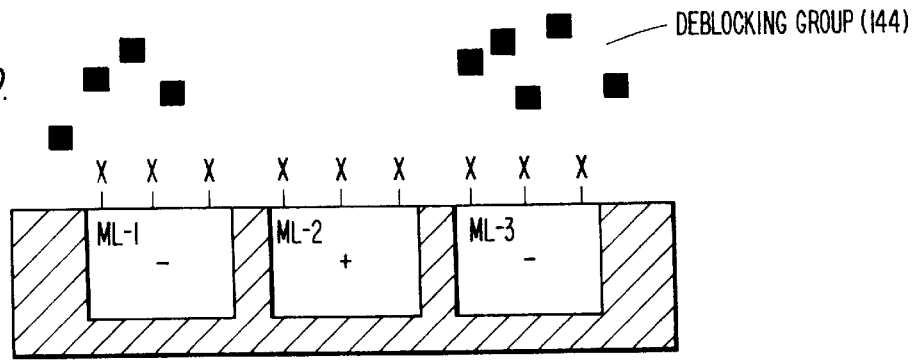
Figure 14C:
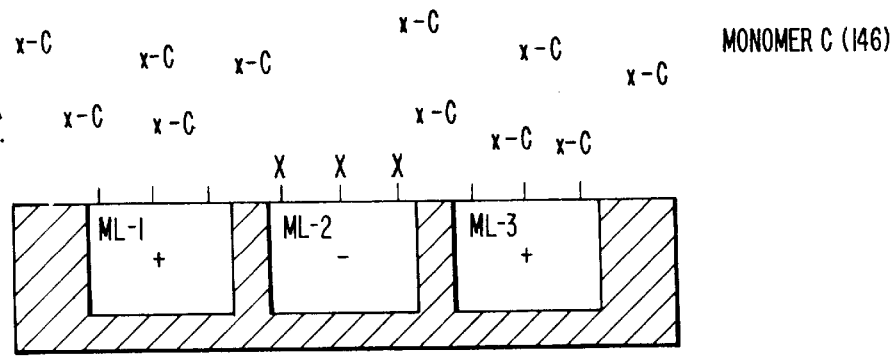
Figure 14D:
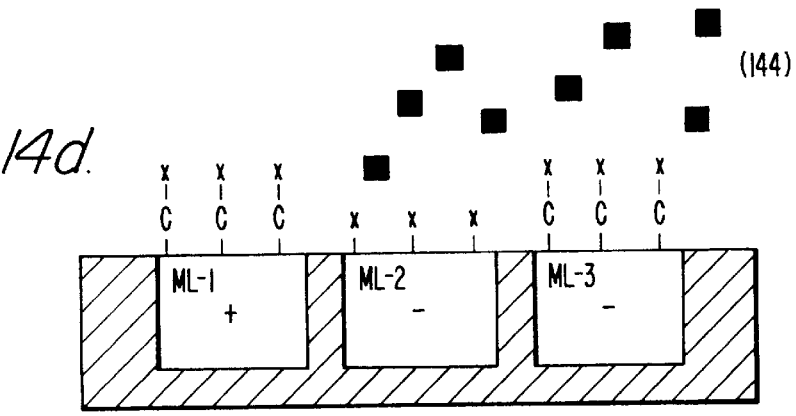
Figure 14E:
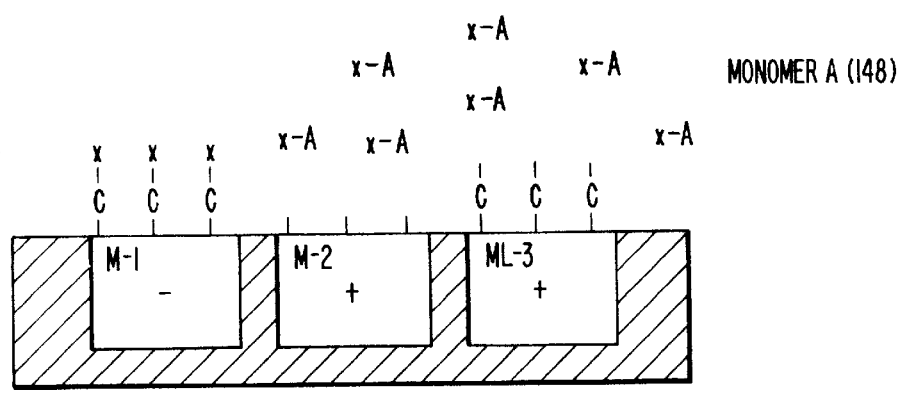
Figure 14F:
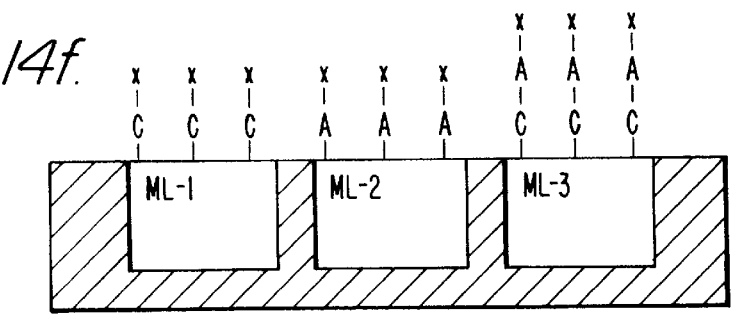

At the second de-blocking step (FIG. 14(D)), those electrode positions which are to be coupled with the next base are made negative, and those which are to remain protected are made positive. The system is now exposed to the next base to be coupled, in this case (x-A) (148), and selective coupling to the de-blocked micro-location is achieved (FIG. 14(E) and (F)). The coupling and deblocking procedures are repeated, until all the different DNA sequences have been synthesized on each of the addressable micro-location surfaces.

The above example represents one possible approach for the synthesis of nucleic acids. Another approach involves a complete water soluble DNA synthesis. In this case, charged water soluble coupling agents, such as 1-ethyl-3-(3-dimethylaminopropyl) carbodiimide (EDCA), is used to carry out oligonucleotide synthesis with water soluble nucleotide derivatives. This approach would have significant advantages over present organic solvent based methods which require extensive blocking of the base moieties. Water soluble synthesis would be less expensive and eliminate the use of many toxic substances used in the present organic solvent based processes. A third approach involves the use of charged monomers.

In addition to DNA synthesis, a similar process can be developed for peptide synthesis, and other complex polymers. Examples contemplated in this disclosure represent the initial potential for this technique, and are based on organic solvent based synthetic procedures for DNA or peptide synthesis.

The recipes for buffers, solutions, and media in the following examples are described in J. Sambrook, E. F. Fritsch, and T. Maniatis, *Molecular Cloning: A Laboratory Manual*, 2 Ed., Cold Spring Harbor Laboratory Press, Cold Spring Harbor, N.Y., 1989.

EXAMPLE 1

Oligomer Reagents

Synthetic DNA probes were made using conventional phosphoramidite chemistry on Applied Biosystems automated DNA synthesizers. Oligomers were designed to contain either a 5' amino or a 3' ribonucleoside terminus. The 5' functionality was incorporated by using the ABI Aminolink 2 reagent and the 3' functionality was introduced by initiating synthesis from an RNA CPG support. The 3' ribonucleotide terminus can be converted to a terminal dialdehyde by the periodate oxidation method which can react with primary amines to form a Schiff's base. Reaction conditions were as follows: Dissolve 20–30 O.D. oligomer in water to a final concentration of 1 OD/$\mu$l. Add 1 vol of 0.1M sodium acetate, pH 5.2 and 1 vol 0.45M sodium periodate (made fresh in water). Stir and incubate reaction for at least 2 hours at ambient temperature, in the dark. Load reaction mix onto a Sephadex G-10 column (pasteur pipette, 0.6×5.5 cm) equilibrated in 0.1M sodium phosphate, pH 7.4. Collect 200 $\mu$l fractions, spot 2 $\mu$l aliquots on thin layer chromatography (TLC) and pool ultra violet (UV) absorbing fractions.

The following oligomers contain 3' ribonucleoside termini (U):
ET12R 5'-GCT AGC CCC TGC TCA TGA GTC TCU
CP-1 5'-AAA AAA AAA AAA AAA AAA AAU
AT-A1 5'-CTA CGT GGA CCT GGA GAG GAA GGA GAC TGC CTG U
AT-A2 5'-GAG TTC AGC AAA TTT GGA GU
AT-A3 5'-CGT AGA ACT CCT CAT CTC CU
AT-A4 5'-GTC TCC TTC CTC TCC AGU
AT-A5 5'-GAT GAG CAG TTC TAC GTG GU
AT-A6 5'-CTG GAG AAG AAG GAG ACU
AT-A7 5'-TTC CAC AGA CTT AGA TTT GAC U
AT-A8 5'-TTC CGC AGA TTT AGA AGA TU
AT-A9 5'-TGT TTG CCT GTT CTC AGA CU
AT-A10 5'-CAT CGC TGT GAC AAA ACA TU Oligomers containing 5' amine groups were generally reacted with fluorophores, such as Texas Red (TR, ex. 590 nm, em. 610 nm). Sulfonyl chlorides are very reactive towards primary amines forming a stable sulfonamide linkage. Texas Red-DNA conjugates were made as follows: Texas Red sulfonyl chloride (Molecular Probes) was dissolved in dimethyl formamide (DMF) to a final concentration of 50 mg/ml (80 mM). Oligomer was dissolved in 0.4M sodium bicarbonate, pH 9.0–9.1, to a final concentration of 1 O.D./$\mu$l (5.4 mM for a 21-mer). In a micro test tube, 10 $\mu$l oligomer and 20 $\mu$l Texas Red was combined. Let reaction proceed in the dark for 1 hour. Quench reaction with ammonia or hydroxylamine, lyophilize sample and purify by PAGE (Sambrook et al., 1989, supra).

The following oligomers contain 5' amino termini:
ET21A 5'-Aminolink2-TGC GAG CTG CAG TCA GAC AT
ET10AL 5'-Aminolink2-GAG AGA CTC ATG AGC AGG
ET11AL 5'-Aminolink2-CCT GCT CAT GAG TCT CTC
T2 5'-Aminolink2-TTT TTT TTT TTT TTT TTT TT
RC-A1 5'-Aminolink2-CAG GCA GTC TCC TTC CTC TCC AGG TCC ACG TAG
RC-A2 5'-Aminolink2-CTC CAA ATT TGC TGA ACT C
RC-A3 5'-Aminolink2-GGA GAT GAG GAG TTC TAC G
RC-A4 5'-Aminolink2-CTG GAG AGG AAG GAG AC
RC-A5 5'-Aminolink2-CCA CGT AGA ACT GCT CAT C
RC-A6 5'-Aminolink2-GTC TCC TTC TTC TCC AG
RC-A7 5'-Aminolink2-GTC AAA TCT AAG TCT GTG GAA
RC-A8 5'-Aminolink2-ATC TTC TAA ATC TGC GGA A
RC-A9 5'-Aminolink2-GTC TGA GAA CAG GCA AAC A
RC-A10 5'-Aminolink2-ATG TTT TGT CAC AGC GAT G

EXAMPLE 2

Electronically Addressable Micro-locations on a Microfabricated Device—Polylysine Method Microelectrodes were fabricated from microcapillary tubes (0.2 mm×5 mm). The microcapillaries were filled with 18–26% polyacrylamide containing 0.1–1.0% polylysine and allowed to polymerize. The excess capillary was scored and removed to prevent air bubbles from being trapped within the tubes and to standardize the tube length. Capillaries were mounted in a manner such that they shared a common upper buffer reservoir and had individual lower buffer reservoirs. Each lower buffer reservoir contained a platinum wire electrode.

The top surface of the microcapillary in the upper reservoir was considered to be the addressable micro-location. Upper and lower reservoirs were filled with 0.1M sodium phosphate, pH 7.4 and prerun for 10' at 0.05 mA constant using a BioRad 500/1000 power supply. Pipette 2 $\mu$l (0.1 O.D.) periodate oxidized ET12R into the upper reservoir while the power is on and electrophorese for 2–5 minutes at constant current. Reverse the polarity so that the test capillary is now biased negative and electrophorese an additional 2–5 minutes. Unbound DNA is repulsed while the covalently attached DNA remains.

Aspirate upper reservoir buffer and rinse with buffer. Disassemble apparatus and mount a fresh reference capillary. Refill reservoir and add fluorescently labeled complement DNA, i.e., ET10AL-TR. E ectrophoretically concentrate the oligomer at the positively biased test micro-location for 2–5 minutes at 0.05 mA constant. Reverse the polarity and remove unbound complement. Remove test capillary and examine by fluorescence. Negative control for nonspecific binding was performed as described above substituting a noncomplementary DNA sequence ET21A-TR for ET10AL-TR.

A cross-section of the capillary micro-locations were examined under a Jena epifluorescent microscope fitted with a Hamamatsu ICCD camera imaging system. Fluorescent results indicate that complement ET10AL-TR hybridized to the binding entity/capture sequence and remained hybridized even when the potential was changed to negative. ET21A-TR noncomplement was not retained at the test capillary when the potential was reversed.

EXAMPLE 3
Electronically Addressable Micro-locations on a Microfabricated Device—Succinimidyl Acrylate Method This example describes an alternative attachment chemistry which covalently binds the 5' terminus of the oligomer. Capillaries were fabricated as described above except that 1% succinimidyl acrylate (Molecular Probes) was substitute for the polylysine. The capillaries were made fresh because the succinimidyl ester reacts with primary amines and is labile, especially above pH 8.0. The capillaries were mounted as described above and the reservoirs were filled with 0.1M sodium phosphate, pH 7.4. Prerun the capillaries for 10 minutes at 0.05 mA. Pipette 2 μl ET10AL (0.1 O.D.), which contains a 5' amino terminus, into the upper reservoir while the power is on and electrophorese for 2–5 minutes. Reverse polarity so that the test capillary is now biased negative and electrophorese an additional 2–5 minutes. Unbound DNA is repulsed while the covalently attached DNA remains.

Aspirate upper reservoir buffer and rinse with buffer. Unmount the reference capillary and mount a fresh reference capillary. Refill reservoir and add fluorescent labeled complement oligomer, ET11AL-TR and electrophorese as described above. Negative control for nonspecific binding was performed as described above substituting a non-complement DNA sequence ET21A-TR for ET11AL-TR.

Fluorescent results indicate that complement ET11AL-TR hybridized to the capture sequence and remained hybridized even when the potential was changed to negative. ET21A-TR noncomplement was not retained at the working capillary when the potential was reversed.

EXAMPLE 4
Electronically Controlled Fluorescent Dye Detection Process-PAGE

DNA dyes such as ethidium bromide (EB) become fluorescent when intercalated into DNA. The fluorescence and binding affinity is greater when the DNA is double stranded than single stranded. Prepare capillaries as in Example 1 and hybridize as described above. EB was added to the solution (~0.05 mM EB final concentration) and the test capillary was biased negative because EB is positively charged. The capillaries were observed by epifluorescence at 550 nm excitation and 600+ nm emission. Both the hybridized and unhybridized micro-locations showed red fluorescence (from EB).

The capillaries were re-mounted biased positive to repulse EB. Maintain constant current at 0.05 mA for 0.03 Volt-Hours.

| Capture | Target | Normalized Signal |
| --- | --- | --- |
| ET10AL | ET11AL (Pos.) | >200 |
| ET10AL | ET21A (Neg.) | 1 |

Fluorescence at the unhybridized micro-locations diminished while the hybridized capillary retained fluorescence. Fluorescent signal was measured using an ICCD camera imaging system and represent peak fluorescent intensities. The signal to noise ratio would be >>1000 fold if the entire fluorescent signal area was integrated. This demonstrates a method for increasing signal to noise ratios and thus the dynamic range of the assay.

EXAMPLE 5
Electronically Addressable Locations on Metal Substrates

Aluminum (Al) and gold (Au) wire (0.25 mm, Aldrich) was reacted with 10% 3-aminopropyltriethoxysilane (APS) in toluene. The APS reagent reacts readily with the oxide and/or hydroxyl groups on the metal surface to form covalent bonds between the oxide and/or hydroxyl groups and the primary amine groups. No pretreatment of the aluminum was necessary. The gold wire was subjected to electrolysis in 5×SSC solution to form an oxide layer. Alternatively the metal wire can be oxidized by a perchloric acid bath.

The APS reaction was performed as follows: Wires were cut to 3 inches and placed in a glass dish. Toluene was added to completely cover the wires and the temperature was brought to 50–60° C. on a heat plate. APS was added to a final concentration of 10%. Mix solution and continue the reaction for 30 minutes. Rinse 3 times with copious volumes of toluene, then rinse 3 times with copious volumes of alcohol and dry in 50° C. oven. The APS treated wire can then be reacted with an aldehyde to form a Schiff's base. Binding entity ET12R was periodate oxidized as described elsewhere. The electrodes were placed in a reservoir of degassed water. Power was applied at 0.05 mA constant for about 30 seconds. Activated ET12R was immediately added. Power was applied, the liquid was aspirated and fresh water was added and then aspirated again. The test (biased positive) and reference electrodes were placed in Hybridization Buffer (HB, 5×SSC, 0.1% SDS) containing fluorescent labeled complement DNA, ET10-TR. After 2 minutes the electrodes were washed three times for one minute each in Wash Buffer (1×SSC, 0.1% SDS) and observed by fluorescence (ex. 590 nm, em. 610 nm).

Results demonstrate that ET12R was specifically coupled to the treated metal surfaces. The test electrode was fluorescent while the reference electrode was not. Nonspecific adsorption of the DNA to the metal was prevented by the presence of SDS in the Hybridization Buffer. Attachment to gold substrates by electrolysis and subsequent APS treatment was effective. Signal obtained was significantly stronger than observed with non-oxidized gold. More importantly, this example showed that the metal surfaces could be chemically functionalized and derivatized with a binding entity and not become insulated from the solution. The APS method represents one of many available chemistries to form DNA-metal conjugates.

EXAMPLE 6
Electronically Controlled Fluorescent Dye Detection Process—Metal Wire DNA-aluminum electrode substrates were prepared and hybridized as described in Example 5. A hybridized and an unhybridized DNA-Al electrode were processed with an underivatized Al wire as the reference. EB was added to the solution and the test DNA electrodes were biased negative to attract the dye. The solution was aspirated and fresh buffer was added. The metal surfaces were examined under the microscope.

Remount the device and apply a positive potential for a defined volt-hour. The buffer was aspirated, the electrodes were observed by epifluorescence. This was repeated until there was a significant difference in fluorescence between the hybridized and unhybridized metal surfaces.

| Capture | Target | Normalized Signal |
| --- | --- | --- |
| ET12R | ET10AL (Pos.) | >140 |
| ET12R | None (Neg.) | 1 |

Fluorescence at the unhybridized metal surfaces diminished while the hybridized metal surfaces retained fluorescence. Fluorescent signal was measured using an ICCD camera imaging system and represent peak fluorescent intensities. The signal to noise ratio would be >>1000 fold if the entire fluorescent signal area was integrated. This example demonstrates a method for increasing signal to noise ratios and thus the dynamic range of the assay. Similar results were obtained using capillary gel configuration, suggesting that electrochemical effects do not significantly affect the performance of the assay.

EXAMPLE 7
Active Programmable Electronic Matrix (APEX)—Micromachine Fabrication

A radial array of 6 addressable 250 μm capillary locations was micro-machined. The device has a common upper reservoir and separate lower reservoirs such that the potential at each micro-location is individually addressable. A unique oligomer binding entity is localized and coupled to a specific capillary micro-location by the methods described elsewhere. The test macro-location has a positive potential while the other micro-locations have negative potentials to prevent nonspecific interactions.

The array is washed and then hybridized with a complementary fluorescently labeled DNA probe. The array is washed to remove excess probe and then observed under an epifluorescent microscope. Only the specifically addressed micro-location will be fluorescent. The process may be repeated with another binding entity at another location and verified by hybridization with a probe labeled with another fluorescent moiety.

DNA sequences are specifically located to predetermined positions with negligible crosstalk with the other locations. This enables the fabrication of micromatrices with several to hundreds of unique sequences at predetermined locales.

EXAMPLE 8
Active, Programmable Electronic Matrix (APEX)—Microlithographic Fabrication An 8×8 matrix of 50 μm square aluminum electrode pads on a silicon wafer (see FIG. 3) was designed, fabricated and packaged with a switch box (see Device Fabrication Section for details). Several materials and process improvements, as described below, were made to increase the selectivity and effectiveness of the chip.

8a) Selection of Topcoat

The APS process involves the entire chip. Selectivity of the functionalization process was dependent on the reactivity of the chip surfaces. In order to reduce functionalization and subsequent DNA attachment of the areas surrounding the micro-locations, a material that is less reactive to APS than $SiO_2$ or metal oxide is needed. Photoresists and silicon nitride were tried. The different topcoats were applied to silicon dioxide chips. The chips were examined by epifluorescence and then treated with APS followed by covalent attachment of periodate oxidized polyA RNA sequences (Sigma, MW 100,000). The chips were hybridized with 200 nM solution of Texas Red labeled 20-mer (T2-TR) in Hybridization Buffer, for 5 minutes at 37° C. The chips were washed 3 times in WB and once in 1×SSC. The chips were examined by fluorescence at 590 nm excitation and 610 nm emission.

Silicon nitride was chosen because it had much less reactivity to APS relative to silicon dioxide and was not inherently fluorescent like the photoresist tested. Other methods such as UV burnout of the background areas are also possible.

8b) APEX Physical Characterization

A finished matrix chip was visually examined using a Probe Test Station (Micromanipulator Model 6000) fitted with a B & L microscope and a CCD camera. The chip was tested for continuity between the test pads and the outer contact pads. This was done by contacting the pads with the manipulator probe tips which were connected to a multimeter. Continuity ensures that the pads have been etched down to the metal surface. The pads were then checked for stability in electrolytic environments. The metal wires were rated to handle up to 1 mA under normal dry conditions. However, reaction to a wet environment was unknown. A drop (1–5 μl) of buffered solution (1×SSC) was pipetted onto the 8×8 matrix. Surface tension keeps the liquid in place leaving the outer contact pad area dry. A probe tip was contacted to a contact pad and another probe tip was contacted with the liquid. The current was incremented up to 50 nA at max voltage of 50 V using a HP 6625A power supply and HP3458A digital multimeter.

The initial fabrication consisted of the silicon substrate, a silicon dioxide insulating layer, aluminum deposition and patterning, and a silicon nitride topcoat. These chips were not very stable in wet environments because the metal/nitride interface was physical in nature and electrolysis would undermine the nitride layer. This would result in the pads being electrically shorted. Furthermore, silicon nitride and Al have different expansion coefficients such that the nitride layer would crack when current was applied. This would allow solution to contact the metal directly, again resulting in electrolysis which would further undermine the layer.

The second fabrication process included a silicon dioxide insulating layer between the aluminum metal and silicon nitride layers. Silicon dioxide and Al have more compatible physical properties and form a better chemical interface to provide a more stable and robust chip.

8c) DNA Attachment

A matrix chip was functionalized with APS reagent as described in Example 5. The chip was then treated with periodate oxidized polyA RNA (Sigma, average MW 100, 000). The chip was washed in WB to remove excess and unbound RNA. This process coated the entire chip with the capture sequence with a higher density at the exposed metal surfaces than at the nitride covered areas. The chip was hybridized with a 200 nM solution of T2-TR in HB for 5 minutes at 37° C., and then washed 3 times in WB and once in 1×SSC for one minute each at ambient temperature. The chip was examined by fluorescence at 590 nm excitation and 610 nm emission.

The opened metal areas were brightly fluorescent and had the shape of the pads. Low fluorescent intensities and/or irregular borders would suggest that the pads were not completely opened. Additional plasma etch times would be recommended.

8d) Electronically Controlled Hybridization

Active hybridization was performed by using a chip from Example 8c and biasing one micro-location positive. This was done by using the switch box which would also automatically bias the remaining micro-locations negative or by using an external solution electrode. Three micro-liters of water was deposited on the matrix pads only. A current, ~1–5 nA, was applied for several seconds and 0.1 pmole of T2-TR was added to the solution. The liquid was removed and the chip was dried and examined by fluorescence at Texas Red wavelengths (ex.590 nm, em.610 nm).

Only the positively biased micro-location was fluorescent. This can be repeated many times to hybridize other micro-locations selectively. Additionally, the fluorescence DNA at one micro-location can be translocated to another micro-location by biasing the initial location negative and the destination positive.

8e) Electronically Controlled Addressing and Device Fabrication

The matrix was functionalized with APS as described above. Binding entity CP-1 was activated by periodate oxidation method. Four micro-locations were biased positive in the matrix and the remainder were biased negative. Two microliters of water was deposited on the matrix and a current was applied. Binding entity, CP-1, was added and allowed to concentrate at the designated locations. The liquid was removed, the chip was rinsed briefly with water and two microliters of water was deposited on the chip. Again, current was applied for several seconds and 0.1 pmole of T2-TR was added. The liquid was removed after a short time and the entire chip was washed in WB, 3 times. The chip was dried and examined for fluorescence.

Results indicate that the positively biased micro-locations were fluorescent. This example demonstrates the selective addressing of micro-locations with a specific binding entity, the localization and covalent coupling of sequences to the micro-locations, and the specific hybridization of complementary target sequences to the derivatized micro-locations.

8f) Genetic Typing APEX Chip

DNA binding entities with 3' ribonucleoside termini are synthesized which are specific for the polymorphisms of HLA gene dQa. The binding entities are activated by periodate oxidation as described above. The reverse complements are also synthesized with 5' amino termini and are conjugated with fluorophores, such as Texas Red, Rhodamine or Bodily dyes, as described elsewhere. The micro-locations are functionalized with primary amines by treatment with APS, as described elsewhere. A couple microliters of solution are placed over the matrix but leaving the contact pads dry. A specific micro-location is addressed by biasing that micro-location positive, the periodate oxidized DNA oligomer is added, ~0.1 pmole, and is translocated and covalently coupled to that location. The polarity is reversed and the unbound binding entity molecules are removed. This is repeated for another binding entity at another addressed micro-location until all the unique binding entities are bound to the chip. The chip is then hybridized to individual fluorescently labeled complement sequences to determine the specificity of the coupling reaction as well as en masse to visualize all addressed micro-locations at once. On the same chip which is denatured to remove complementary oligomers (10 minutes at 90° C. in 0.05% SDS), the addressed micro-locations are hybridized with unlabeled reverse complements or genomic DNA. Detection is via the fluorescent dye detection assay as described elsewhere.

Results will demonstrate that micro-locations are specifically addressed with unique binding entities. Nonspecific binding to negatively biased micro-locations will be negligible. The device and associated binding entity chemistry is stable under denaturation conditions, thus making the addressed and fabricated device reusable. Alternative methods for denaturing the hybrids would be to increase the current and/or increase the time it is applied.

EXAMPLE 9

Electronic Stringency Control

The ability of the device to affect electronic stringency control is demonstrated with the Ras oncogene model system. A single base pair mismatch adversely affects the melting temperature (Tm), a measure of the stability of the duplex. Traditional methods to discriminate between mismatch and perfect match (i.e., stringency control) rely on temperature and salt conditions. Stringency can also be affected by the electrophoretic potential. Oligomers listed below can be paired such that resulting hybrids have 0–2 mismatches. Oligomer binding entities are coupled to the micro-location and hybridized as described elsewhere. The polarity at the micro-location is then reversed and the hybrids are subjected to constant current for a given time, or defined power levels to denature the mismatch without affecting the perfect match.

Ras-G 5'-GGT GGT GGG CGC CGG CGG TGT GGG CAA GAU -3'
Ras-1 3'-CC GCG GCC GCC ACA C-Aminolink2-5'
Ras-2 3'-CC GCG GCA GCC ACA C -Aminolink2-5'
Ras-3 3'-CC GTG GCA GCC ACA C -Aminolink2 -5'
Ras-T 5'-GGT GGT GGG CGC CGT CGG TGT GGG CAA GAU -3'

Microelectrodes are fabricated from microcapillary tubes as described elsewhere. Binding entities Ras-G is periodate oxidized and covalently bound to the addressed micro-location. Ras-G micro-location is then hybridized with Ras-1-TR which is the perfect match., Ras-2-TR which is a one base pair mismatch (G-A) or Ras-3-TR which is a two base pair mismatch (G-A and G-T). The micro-locations are examined fluorescently to verify whether complementary sequences are hybridized and to what extent. The microcapillaries are re-mounted and subjected to controlled time at constant current until the mismatched hybrids are removed without significantly affecting the perfectly matched hybrids.

Results will indicate that stringency could be affected by the electrophoretic potential. This example demonstrates that each micro-location can have individual stringency control, thus overcomes a major obstacle to large scale parallel processing techniques which had been limited to a single common stringency level.

What is claimed is:

1. An electronically controlled method for combinatorial synthesis of a biopolymer, comprising the steps of:

provinding a plurality of reaction locations on a substrate, each reaction location being individually electronically addressable;

providing an attachment layer upon at least some reaction locations;

placing said reaction locations in contact with a solution containing a charged monomer-A;

selectively biasing those locations at which monomer A is to react at an opposite charge to monomer-A, and biasing those locations at which monomer A is not to react at the same charge as monomer-A;

concentrating and reacting monomer A on the specific A locations;

removing unreacted monomer A;

providing said reaction locations in contact with charged monomer B;

selectively biasing those locations for which monomer B is to react at the opposite charge of monomer-B, and biasing those locations at which monomer B is not to react at the same charge as monomer-B;

concentrating and reacting monomer B on the specific B locations;

removing unreacted monomer B, and repeating the process with monomers until all biopolymer sequences are complete.

2. The methods of claim 1 for electronically controlled combinatorial synthesis of a biopolymer wherein at least one biopolymer includes an oligonucleotide.

3. The method of claim 2 for electronically controlling, combinatorial synthesis of a biopolymer wherein the oligonucleotide is a deoxyribonucleic acid (DNA).

4. The method of claim 1 for electronically controlling the combinatorial synthesis of a biopolymer wherein at least one biopolymer includes a peptide.

5. The method of claim 1 for electronically controlling combinatorial synthesis of a biopolymer wherein at least one biopolymer is a complex polymer.

6. A method for synthesizing a plurality of polymers, the polymers being composed of monomers in selected positions, at a plurality of locations on an active, programmable electronic matrix device, comprising the steps of:

providing a selected charged reactant on the device adjacent the locations, synthesizing the polymer by selectively:

biasing those locations attractive to the charged reactant where the polymer includes a specified monomer at the selected position, and simultaneously biasing those locations repulsive to the charged reactant where the polymer does not include the specified monomer at said selected position, selectively reacting the specified monomer, and repeating the above steps by sequentially providing charged reactants to the device, and biasing the locations attractive and repulsive to include or exclude, respectively, a monomer at the selected positions.

7. The method of claim 6 for synthesizing a polymer wherein the charged reactant is a charged deblocking reagent.

8. The method of claim 7 for synthesizing a polymer wherein after the charged deblocking reagent has been attracted to the location, the said specifed monomer is provided at the location.

9. The method of claim 6 for synthesizing a polymer wherein the charged reactant is a charged coupling reagent.

10. The method of claim 9 for synthesizing a polymer wherein after the charged coupling reagent has been attracted to the location, the said monomer is provided at the location.

11. The method of claim 9 for synthesizing a polymer wherein the charged coupling reagent is water soluble.

12. The method of claim 6 for synthesizing a polymer wherein the charged reactant includes said specified monomer.

13. The method of claim 6 for synthesizing a polymer wherein at least one polymer includes an oligonucleotide.

14. The method of claim 13 for synthesizing a polymer wherein the oligonucleotide is DNA.

15. The method of claim 6 for synthesizing a polymer wherein at least one polymer includes a peptide.

16. The method of claim 6 for synthesizing a polymer wherein the polymer is a complex polymer.

17. The method of claim 6 for synthesizing a polymer wherein the charged reactant has a net positive charge.

18. The method of claim 6 for synthesizing a polymer wherein the charged reactant has a net negative charge.

19. The method of claim 6 for synthesizing a polymer wherein the charged reactants are provided with a net charge.

20. The method of claim 6 for synthesizing a polymer further including the step of removing the unreacted charged reactant.

21. The method of claim 6 for synthesizing a polymer wherein the locations are selected to be micro-locations.

22. The method of claim 6 for synthesizing a polymer further including the step of electronically delivering reactants from an electronic reagent supply device.

* * * * *

UNITED STATES PATENT AND TRADEMARK OFFICE
CERTIFICATE OF CORRECTION

PATENT NO. : 5,929,208
DATED : July 27, 1999
INVENTOR(S) : Michael J. Heller and Eugene Tu It is certified that error appears in the above-identified patent and that said Letters Patent is hereby corrected as shown below:

Column 7,
Line 7, delete "inventions" and insert therefor -- invention --.
Line 11, delete "eletrode" and insert therefor -- electrode --.

Column 8,
Line 30, delete "electronicaLly" and insert therefor -- electronically --.

Column 10,
Line 6, delete "suLtable" and insert therefor -- suitable --.
Line 46, delete "microeletrode" and insert therefor -- microelectrode --.
Line 63, delete "nanometers" and insert therefor -- nanometer --.

Column 12,
Lines 25-26, delete:
"FABRICATION PROCEDURES (MICROLITHOGRAPHY)"
and insert therefor -- FABRICATION PROCEDURES (MICROLITHOGRAPHY) --

Column 17,
Line 22, delete "eletrodes" and insert therefor -- electrodes --.

Column 28,
Line 13, delete "(Tm) ," and insert therefor -- (Tm ), --.

Signed and Sealed this

Thirtieth Day of October, 2001

*Attest:*

NICHOLAS P. GODICI
*Attesting Officer*  Acting Director of the United States Patent and Trademark Office

SEQUENCE LISTING (1) GENERAL INFORMATION:

(iii) NUMBER OF SEQUENCES:31

(2) INFORMATION FOR SEQ ID NO:1:

(i) SEQUENCE CHARACTERISTICS:
      (A) LENGTH:24
      (B) TYPE:nucleic acid
      (C) STRANDEDNESS:single
      (D) TOPOLOGY:linear (ii) SEQUENCE DESCRIPTION: SEQUENCE ID NO: 1:

GCTAGCCCCT GCTCATGAGT CTCU                                      24

(2) INFORMATION FOR SEQ ID NO:2:

(i) SEQUENCE CHARACTERISTICS:
        (A) LENGTH:21
        (B) TYPE:nucleic acid
        (C) STRANDEDNESS:single
        (D) TOPOLOGY:linear (ii) SEQUENCE DESCRIPTION: SEQUENCE ID NO: 2:

AAAAAAAAAA AAAAAAAAAA U                                         21

(2) INFORMATION FOR SEQ ID NO:3:

(i) SEQUENCE CHARACTERISTICS:
        (A) LENGTH:34
        (B) TYPE:nucleic acid
        (C) STRANDEDNESS:single
        (D) TOPOLOGY:linear (ii) SEQUENCE DESCRIPTION: SEQUENCE ID NO: 3:

CTACGTGGAC CTGGAGAGGA AGGAGACTGC CTGU                            34

(2) INFORMATION FOR SEQ ID NO:4:

(i) SEQUENCE CHARACTERISTICS:
        (A) LENGTH:20
        (B) TYPE:nucleic acid
        (C) STRANDEDNESS:single
        (D) TOPOLOGY:linear (ii) SEQUENCE DESCRIPTION: SEQUENCE ID NO: 4:

GAGTTCAGCA AATTTGGAGU                                           20

(2) INFORMATION FOR SEQ ID NO:5:

(i) SEQUENCE CHARACTERISTICS:
        (A) LENGTH:20
        (B) TYPE:nucleic acid
        (C) STRANDEDNESS:single
        (D) TOPOLOGY:linear (ii) SEQUENCE DESCRIPTION: SEQUENCE ID NO: 5:

CGTAGAACTC CTCATCTCCU                                           20

(2) INFORMATION FOR SEQ ID NO:6:

(i) SEQUENCE CHARACTERISTICS:
        (A) LENGTH:18
        (B) TYPE:nucleic acid
        (C) STRANDEDNESS:single
        (D) TOPOLOGY:linear (ii) SEQUENCE DESCRIPTION: SEQUENCE ID NO: 6:

GTCTCCTTCC TCTCCAGU                                             18

(2) INFORMATION FOR SEQ ID NO:7:

(i) SEQUENCE CHARACTERISTICS:
        (A) LENGTH:20
        (B) TYPE:nucleic acid
        (C) STRANDEDNESS:single
        (D) TOPOLOGY:linear (ii) SEQUENCE DESCRIPTION: SEQUENCE ID NO: 7:

GATGAGCAGT TCTACGTGGU                                           20

(2) INFORMATION FOR SEQ ID NO:8:

(i) SEQUENCE CHARACTERISTICS:
        (A) LENGTH:18
        (B) TYPE:nucleic acid
        (C) STRANDEDNESS:single
        (D) TOPOLOGY:linear (ii) SEQUENCE DESCRIPTION: SEQUENCE ID NO: 8:

CTGGAGAAGA AGGAGACU                                      18

(2) INFORMATION FOR SEQ ID NO:9:

(i) SEQUENCE CHARACTERISTICS:
        (A) LENGTH:22
        (B) TYPE:nucleic acid
        (C) STRANDEDNESS:single
        (D) TOPOLOGY:linear (ii) SEQUENCE DESCRIPTION: SEQUENCE ID NO: 9:

TTCCACAGAC TTAGATTTGA CU                                22

(2) INFORMATION FOR SEQ ID NO:10:

(i) SEQUENCE CHARACTERISTICS:
        (A) LENGTH:20
        (B) TYPE:nucleic acid
        (C) STRANDEDNESS:single
        (D) TOPOLOGY:linear (ii) SEQUENCE DESCRIPTION: SEQUENCE ID NO: 10:

TTCCGCAGAT TTAGAAGATU                                  20

(2) INFORMATION FOR SEQ ID NO:11:

(i) SEQUENCE CHARACTERISTICS:
        (A) LENGTH:20
        (B) TYPE:nucleic acid
        (C) STRANDEDNESS:single
        (D) TOPOLOGY:linear (ii) SEQUENCE DESCRIPTION: SEQUENCE ID NO: 11:

TGTTTGCCTG TTCTCAGACU                                  20

(2) INFORMATION FOR SEQ ID NO:12:

(i) SEQUENCE CHARACTERISTICS:
        (A) LENGTH:20
        (B) TYPE:nucleic acid
        (C) STRANDEDNESS:single
        (D) TOPOLOGY:linear (ii) SEQUENCE DESCRIPTION: SEQUENCE ID NO: 12:

CATCGCTGTG ACAAAACATU                                  20

(2) INFORMATION FOR SEQ ID NO:13:

(i) SEQUENCE CHARACTERISTICS:
        (A) LENGTH:20
        (B) TYPE:nucleic acid
        (C) STRANDEDNESS:single
        (D) TOPOLOGY:linear (ii) SEQUENCE DESCRIPTION: SEQUENCE ID NO: 13:

TGCGAGCTGC AGTCAGACAT                                  20

(2) INFORMATION FOR SEQ ID NO:14:

(i) SEQUENCE CHARACTERISTICS:
        (A) LENGTH:18
        (B) TYPE:nucleic acid
        (C) STRANDEDNESS:single
        (D) TOPOLOGY:linear (ii) SEQUENCE DESCRIPTION: SEQUENCE ID NO: 14:

GAGAGACTCA TGAGCAGG                                                             18

(2) INFORMATION FOR SEQ ID NO:15:

(i) SEQUENCE CHARACTERISTICS:
        (A) LENGTH:18
        (B) TYPE:nucleic acid
        (C) STRANDEDNESS:single
        (D) TOPOLOGY:linear (ii) SEQUENCE DESCRIPTION: SEQUENCE ID NO: 15:

CCTGCTCATG AGTCTCTC                                                             18

(2) INFORMATION FOR SEQ ID NO:16:

(i) SEQUENCE CHARACTERISTICS:
        (A) LENGTH:20
        (B) TYPE:nucleic acid
        (C) STRANDEDNESS:single
        (D) TOPOLOGY:linear (ii) SEQUENCE DESCRIPTION: SEQUENCE ID NO: 16:

TTTTTTTTTT TTTTTTTTTT                                                      20

(2) INFORMATION FOR SEQ ID NO:17:

(i) SEQUENCE CHARACTERISTICS:
        (A) LENGTH:33
        (B) TYPE:nucleic acid
        (C) STRANDEDNESS:single
        (D) TOPOLOGY:linear (ii) SEQUENCE DESCRIPTION: SEQUENCE ID NO: 17:

CAGGCAGTCT CCTTCCTCTC CAGGTCCACG TAG                               33

(2) INFORMATION FOR SEQ ID NO:18:

(i) SEQUENCE CHARACTERISTICS:
        (A) LENGTH:19
        (B) TYPE:nucleic acid
        (C) STRANDEDNESS:single
        (D) TOPOLOGY:linear (ii) SEQUENCE DESCRIPTION: SEQUENCE ID NO: 18:

CTCCAAATTT GCTGAACTC                                                        19

(2) INFORMATION FOR SEQ ID NO:19:

(i) SEQUENCE CHARACTERISTICS:
        (A) LENGTH:19
        (B) TYPE:nucleic acid
        (C) STRANDEDNESS:single
        (D) TOPOLOGY:linear (ii) SEQUENCE DESCRIPTION: SEQUENCE ID NO: 19:

GGAGATGAGG AGTTCTACG                                                        19

(2) INFORMATION FOR SEQ ID NO:20:

(i) SEQUENCE CHARACTERISTICS:
    (A) LENGTH:17
    (B) TYPE:nucleic acid
    (C) STRANDEDNESS:single
    (D) TOPOLOGY:linear (ii) SEQUENCE DESCRIPTION: SEQUENCE ID NO: 20:

CTGGAGAGGA AGGAGAC                                                17

(2) INFORMATION FOR SEQ ID NO:21:

(i) SEQUENCE CHARACTERISTICS:
        (A) LENGTH:19
        (B) TYPE:nucleic acid
        (C) STRANDEDNESS:single
        (D) TOPOLOGY:linear (ii) SEQUENCE DESCRIPTION: SEQUENCE ID NO: 21:

CCACGTAGAA CTGCTCATC                                              19

(2) INFORMATION FOR SEQ ID NO:22:

(i) SEQUENCE CHARACTERISTICS:
        (A) LENGTH:17
        (B) TYPE:nucleic acid
        (C) STRANDEDNESS:single
        (D) TOPOLOGY:linear (ii) SEQUENCE DESCRIPTION: SEQUENCE ID NO: 22:

GTCTCCTTCT TCTCCAG                                                17

(2) INFORMATION FOR SEQ ID NO:23:

(i) SEQUENCE CHARACTERISTICS:
        (A) LENGTH:21
        (B) TYPE:nucleic acid
        (C) STRANDEDNESS:single
        (D) TOPOLOGY:linear (ii) SEQUENCE DESCRIPTION: SEQUENCE ID NO: 23:

GTCAAATCTA AGTCTGTGGA A                                           21

(2) INFORMATION FOR SEQ ID NO:24:

(i) SEQUENCE CHARACTERISTICS:
        (A) LENGTH:19
        (B) TYPE:nucleic acid
        (C) STRANDEDNESS:single
        (D) TOPOLOGY:linear (ii) SEQUENCE DESCRIPTION: SEQUENCE ID NO: 24:

ATCTTCTAAA TCTGCGGAA                                              19

(2) INFORMATION FOR SEQ ID NO:25:

(i) SEQUENCE CHARACTERISTICS:
        (A) LENGTH:19
        (B) TYPE:nucleic acid
        (C) STRANDEDNESS:single
        (D) TOPOLOGY:linear (ii) SEQUENCE DESCRIPTION: SEQUENCE ID NO: 25:

GTCTGAGAAC AGGCAAACA                                              19

(2) INFORMATION FOR SEQ ID NO:26:

(i) SEQUENCE CHARACTERISTICS:
        (A) LENGTH:19

-continued

```
            (B) TYPE:nucleic acid
            (C) STRANDEDNESS:single
            (D) TOPOLOGY:linear (ii) SEQUENCE DESCRIPTION: SEQUENCE ID NO: 26:

ATGTTTTGTC ACAGCGATG                                                        19

(2) INFORMATION FOR SEQ ID NO:27:

(i) SEQUENCE CHARACTERISTICS:
            (A) LENGTH:30
            (B) TYPE:nucleic acid
            (C) STRANDEDNESS:single
            (D) TOPOLOGY:linear (ii) SEQUENCE DESCRIPTION: SEQUENCE ID NO: 27:

GGTGGTGGGC GCCGGCGGTG TGGGCAAGAU                                            30

(2) INFORMATION FOR SEQ ID NO:28:

(i) SEQUENCE CHARACTERISTICS:
            (A) LENGTH:15
            (B) TYPE:nucleic acid
            (C) STRANDEDNESS:single
            (D) TOPOLOGY:linear (ii) SEQUENCE DESCRIPTION: SEQUENCE ID NO: 28:

CACACCGCCG GCGCC                                                            15

(2) INFORMATION FOR SEQ ID NO:29:

(i) SEQUENCE CHARACTERISTICS:
            (A) LENGTH:15
            (B) TYPE:nucleic acid
            (C) STRANDEDNESS:single
            (D) TOPOLOGY:linear (ii) SEQUENCE DESCRIPTION: SEQUENCE ID NO: 29:

CACACCGACG GCGCC                                                            15

(2) INFORMATION FOR SEQ ID NO:30:

(i) SEQUENCE CHARACTERISTICS:
            (A) LENGTH:15
            (B) TYPE:nucleic acid
            (C) STRANDEDNESS:single
            (D) TOPOLOGY:linear (ii) SEQUENCE DESCRIPTION: SEQUENCE ID NO: 30:

CACACCGACG GTGCC                                                            15

(2) INFORMATION FOR SEQ ID NO:31:

(i) SEQUENCE CHARACTERISTICS:
            (A) LENGTH:30
            (B) TYPE:nucleic acid
            (C) STRANDEDNESS:single
            (D) TOPOLOGY:linear (ii) SEQUENCE DESCRIPTION: SEQUENCE ID NO: 31:

GGTGGTGGGC GCCGTCGGTG TGGGCAAGAU                                            30
```